US007666639B2

(12) United States Patent
Knecht et al.

(10) Patent No.: US 7,666,639 B2
(45) Date of Patent: Feb. 23, 2010

(54) PLANT DEOXYRIBONUCLEOSIDE KINASE ENZYMES AND THEIR USE

(76) Inventors: Wolfgang Knecht, Folkungagatan 7, Göteborg (SE) S-41102; Birgitte Munch-Petersen, Bavnebjergspark 36, Farum (DK) DK-3520; Jure Piskur, Örnvägen 25, Lund (SE) S-22732

( * ) Notice: Subject to any disclaimer, the term of this patent is extended or adjusted under 35 U.S.C. 154(b) by 396 days.

(21) Appl. No.: 10/519,395

(22) PCT Filed: Jun. 24, 2003

(86) PCT No.: PCT/DK03/00429

§ 371 (c)(1),
(2), (4) Date: Oct. 7, 2005

(87) PCT Pub. No.: WO2004/003185

PCT Pub. Date: Jan. 8, 2004

(65) Prior Publication Data

US 2006/0230467 A1    Oct. 12, 2006

(30) Foreign Application Priority Data

Jun. 26, 2002  (DK)  ............................... 2002 00981

(51) Int. Cl.
*C12N 9/00* (2006.01)
*C12N 9/12* (2006.01)
*A61K 38/43* (2006.01)
(52) U.S. Cl. ...................... 435/183; 435/194; 424/94.1; 530/350
(58) Field of Classification Search ................. 435/183, 435/194; 424/94.1; 530/350
See application file for complete search history.

(56) References Cited

U.S. PATENT DOCUMENTS

| | | | |
|---|---|---|---|
| 5,877,010 A | | 3/1999 | Loeb et al. |
| 6,451,571 B1 * | | 9/2002 | Loeb et al. ................. 435/194 |
| 2003/0154513 A1 * | | 8/2003 | Eenennaam et al. ......... 800/281 |
| 2004/0034888 A1 * | | 2/2004 | Liu et al. .................... 800/289 |
| 2007/0044171 A1 * | | 2/2007 | Kovalic et al. .............. 800/278 |

FOREIGN PATENT DOCUMENTS

| | | |
|---|---|---|
| WO | WO 00/36099 A1 | 6/2000 |
| WO | WO 01/88106 A2 | 11/2001 |
| WO | WO 03/100045 A1 | 12/2003 |

OTHER PUBLICATIONS

Guo et al, Proc Natl Acad Sci 101(25):9205-9210, 2004.*
Hult and Berglund, Curr Opin Biotechnol 14:395-400, 2003.*
Munch-Petersen et al, J. Biol. Chem. 273(7):3926-3931, 1998.*
Cleland et al, Apr., Current Opinion in Biotechnology 12: 212-219, 2001.*
Ngo et al. in The Protein Folding Problem and Tertiary Structure Prediction, 1994, Merz et al. (ed.), Birkhauser, Boston, MA.*
Alexandrov et al, EP 1033405 A2 (front page only) and Search Result for SEQ ID No. 6.*
Theologis et al (Database Accession #E96743, Mar. 2, 2001; Sequence alignment available in Score).*
Lin et al (Accession # Q9C7G7_ARATH, Jan. 2001; Sequence alignment available in Score).*
Sasaki et al (Accession # Q8RV55_ORYSJ, Jul. 2001; Sequence alignment available in Score).*
Sadrini et al (Database Accession #Q71F76_SOLLC, May, 2002; Sequence alignment available in Score).*
Eriksson, et al., "Structure and function of cellular deoxyribonucleoside kinases", *Cell. Mol. Life Sci.*, vol. 59, pp. 1327-1346, 2002.
Johansson, et al., "Structural basis for substrate specificities of cellular deoxyribonucleoside kinases", *Nature Structural Biology*, vol. 8, No. 7, pp. 616-620, Jul. 2001.
Botina, T. I et al., Growth Stimulator for potato plants—consists of di sodium slat of adenilyl (2'-5') adenyfyl (2'-5') guanosine, (Jan. 30, 1993), Database WPI, Section Ch, Week 199413, abstract.
Golaszewski, Tomas et al., "Thymidine kinase activity in rye chloroplasts", *FEBS Letters* (Oct. 1975), vol. 58, No. 1, pp. 370-373.
Kunishige, I. et al., "Suicide gene therapy for human uterine adenocarcinoma cells using herpes simplex virus thymidine kinase", (Jan. 1999), Database Accession No. NLM9889024, abstract.
Lin, X. et al., "Arabidopsis thaliana chromosome 1 BAC F28P5 genomic sequence", (Jan. 19, 2001), Database Accession No. AAG51141, abstract and sequence listing.
Sasaki, T. et al, "The genome sequence and structure of rice chromosome 1", (Mar. 29, 2003), Database Accession No. BAB89289, abstract.
Scacchi, A. et al., "Herbicidal activity of dealanylascamycin, a nucleoside antibiotic", (1994), Database Accession No. 1995:227969, abstract.
Strauss, A. et al., "Selective killing of dividing plant cells in culture using nucleoside analogs", (1978), vol. 34, No. 7, p. 958, Abstract, database name NCBI, accession No. XP002270507.
Alcala, J. et al., "generation of ESTs from tomato fruit tissue", (1999), Database Accession No. AW223792, sequence listing.

(Continued)

*Primary Examiner*—Anne Marie Wehbe
*Assistant Examiner*—Kevin K. Hill
(74) *Attorney, Agent, or Firm*—Iver P. Cooper

(57) ABSTRACT

This invention relates to pharmaceutical compositions comprising plant deoxyribonucleoside kinase enzymes (dNK) capable of phosphorylating nucleoside analogs and to medical use of said dNKs. More specifically the invention relates to the medical use of deoxyribonucleoside kinase enzymes derived from (*Arabidopsis thaliana*), from loblolly pine (*Pinus taeda*), from tomato (*Lycopersicum esculentum*), from maize (*Zea mays*) or from rice (*Oryza sativa*). The invention also relates to methods of sensitizing cells to prodrugs, and to methods of inhibiting pathogenic agents in warm-blooded animals using said plant dNKs.

In another aspect the invention relates to plant derived deoxyribonucleoside kinase enzymes provided in isolated form from loblolly pine (*Pinus taeda*), from tomato (*Lycopersicum esculentum*), from maize (*Zea mays*) or from rice (*Oryza sativa*). In further aspects the invention provides polynucleotides encoding the plant dNKs, vector constructs comprising the polynucleotide, packaging cell lines capable of producing said vector, and genetically modified isolated host cells transduced/transfected/-transformed with the vector.

30 Claims, No Drawings

OTHER PUBLICATIONS

Knecht, W. et al., "Identification of Residues Involved in the Specificity and Regulation of the Highly Efficient Multisubstrate Deoxyribonucleoside Kinase from *Drosophila melanogaster*", *J. Mol. Biol.*, (2000), vol. 301, pp. 827-837.

Munch-Petersen, B. et al., "Functional Expression of a Multisubstrate Deoxyribonucleoside Kinase from *Drosophila melanogaster* and Its C-terminal Deletion Mutants", *The Journal of Biological Chemistry*(Mar. 3, 2000), vol. 275, No. 9, pp. 6673-6679.

Sandrini, M. P. B., et al., "New deoxyribonucleoside kinases from plants", (Jan. 1, 2004), Database Accession No. AF514776, sequence listing.

Sasaki, T., et al., "Oryza sativa nipponbare (GA3) genomic DNA, chromosome 1, PAC clone; P0648C09", (Mar. 13, 2002), Database Accession No. AP003922, abstract and sequence listing.

Walbot, V., "Maize ESTs from various cDNA libraries sequenced at Stanford University", (Sept. 14, 1999), Database Accession No. AW36847, sequence listing.

Whetten, R. W., et al., "The Pine Gene Discovery Project", (Sept 9, 1999), Database Accession No. AW011158, abstract and sequence listing.

Yamamoto, K. et al., Rice cDNA from panicle (longer than 10cm), Sep. 23, 1997), sequence listing.

Sasaki, T., "Rice cDNA from panicle (longer than 10cm) Oryza sativa Japonica Group cDNA clone E20702_1A, mRNA sequence", entry created Sept. 23, 1997, Database Accession No. C73813, sequence listing.

Piskur, deoxynucleoside kinase [*Drosophila melanogaster*] "first seen by NCBI", May 4, 1999, "INV Mar. 3, 2000", Database Accession No. CAB41881, sequence listing.

\* cited by examiner

US 7,666,639 B2

PLANT DEOXYRIBONUCLEOSIDE KINASE ENZYMES AND THEIR USE

TECHNICAL FIELD

This invention relates to pharmaceutical compositions comprising plant deoxyribonucleoside kinase enzymes (dNK) capable of phosphorylating nucleoside analogs and to medical use of said dNKs. More specifically the invention relates to the medical use of deoxyribonucleoside kinase enzymes derived from (*Arabidopsis thaliana*), from loblolly pine (*Pinus taeda*), from tomato (*Lycopersicum esculentum*), from maize (*Zea mays*) or from rice (*Oryza sativa*). The invention also relates to methods of sensitising cells to prodrugs, and to methods of inhibiting pathogenic agents in warm-blooded animals using said plant dNKs.

In another aspect the invention relates to plant derived deoxyribonucleoside kinase enzymes provided in isolated form from loblolly pine (*Pinus taeda*), from tomato (*Lycopersicum esculentum*), from maize (*Zea mays*) or from rice (*Oryza sativa*). In further aspects the invention provides polynucleotides encoding the plant dNKs, vector constructs comprising the polynucleotide, packaging cell lines capable of producing said vector, and genetically modified isolated host cells transduced/transfected/transformed with the vector.

BACKGROUND ART

DNA is made of four deoxyribonucleoside triphosphates, provided by the de novo and the salvage pathway. The key enzyme of the de novo pathway is ribonucleotide reductase, which catalyses the reduction of the 2'-OH group of the nucleoside diphosphates, and the key salvage enzymes are the deoxyribonucleoside kinases, which phosphorylate deoxyribonucleosides to the corresponding deoxyribonucleoside monophosphates.

Deoxyribonucleoside kinases from various organisms differ in their substrate specificity, regulation of gene expression and cellular localisation. In mammalian cells there are four enzymes with overlapping specificities, the thymidine kinases 1 (TK1) and 2 (TK2), deoxycytidine kinase (dCK) and deoxyguanosine kinase (dGK) phosphorylate purine and pyrimidine deoxyribonucleosides. TK1 and TK2 are pyrimidine specific and phosphorylate deoxyuridine (dUrd) and thymidine (dThd), and TK2 also phosphorylates deoxycytidine (dCyd). dCK phosphorylates dCyd, deoxyadenosine (dAdo) and deoxyguanosine (dGuo), but not dThd. dGK phosphorylates dGuo and dAdo. In mammals, TK1 is cytosolic, and TK2 and dGK are localised in the mitochondria, although recent reports indicate a cytoplasmic localisation of TK2 as well.

WO 01/88106 describes multi-substrate deoxyribonucleoside kinase variants derived from insects, in particular *Drosophila melanogaster*, and *Bombyx mori*, and amphibians *Xenopus laevis*.

A piece of genomic DNA from *Arabidopsis thaliana* has been annotated as putative deoxyguanosine kinase (dGK), suggesting that it converts only purine nucleosides, in GenBank™ (Accession No. AAG51141). However, up to this date no experimental work towards characterisation, properties, localisabon, use or biological function of plant kinases has yet been accomplished.

SUMMARY OF THE INVENTION

It is an object of the present invention to provide plant deoxyribonucleoside kinases useful for converting nucleoside analogs into toxic substances, and useful for converting nucleosides into monophosphates. In particular it is an object of the invention to provide such plant deoxyribonucleoside kinases for medical use.

It is a further object to provide pharmaceutical compositions making use of the properties of said plant-derived deoxyribonucleoside kinases.

In a first aspect the invention relates to a pharmaceutical composition comprising at least one plant deoxyribonucleoside kinase enzyme, or a polynucleotide sequence encoding said at least one plant deoxyribonucleoside kinase enzyme, or an expression vector comprising said polynucleotide sequence, or a packaging cell line capable of producing an infective virion comprising said vector, or an isolated host cell transduced with the vector, and a pharmaceutically acceptable carrier or diluent.

Plant deoxyribonucleoside kinases have never been contemplated for use in a pharmaceutical composition or for medical use at all. The present inventors have determined that plant deoxyribonucleoside kinases have properties different from those of deoxyribonucleoside kinases from other taxons, in particular virus and animals, which properties make plant deoxyribonucleoside kinases better for medical use than other deoxyribonucleoside kinases.

Preferably, the plant deoxyribonucleoside kinase enzyme is selected from the group consisting of:
  a plant deoxyribonucleoside kinase enzyme derived from thale cress (*Arabidopsis thaliana*), loblolly pine (*Pinus taeda*), from tomato (*Lycopersicum esculentum*), from maize (*Zea mays*) or from rice (*Oryza sativa*),
  a plant deoxyribonucleoside kinase enzyme comprising the amino acid sequence of SEQ ID NO: 2, SEQ ID NO: 4, SEQ ID NO: 6, SEQ ID NO: 8, SEQ ID NO: 10, or SEQ ID NO: 12,
  a plant deoxyribonucleoside kinase enzyme comprising an amino acid sequence of at least 70% identity with any one of said SEQ ID Nos, when determined over its entire length,
  a plant deoxyribonucleoside kinase enzyme having an amino acid sequence which, when aligned with a sequence selected from those presented in Table 1, comprises 60% or more of the residues identified in Table 1 as conserved residues, and
  a plant deoxyribonucleoside kinase as defined above having a C-terminal and/or N-terminal deletion in the order of 1-80 amino acid residues.

The present inventors have determined that the plant deoxyribonucleoside kinases as defined above have unexpected properties in terms of substrate specificity. This means that the enzymes are essentially multi-substrate, plant dCK/dGK-like kinase enzymes. It also means that the enzymes are more efficient that the known dNKs of which the deoxyribonucleoside kinase derived from human Herpes simplex virus type 1 (HSV-1) is the most promising. For example, upon transduction into a cell, the preferred enzymes of the pharmaceutical compositions decrease at least 3 fold the lethal dose ($LD_{100}$) of at least one nucleoside analogue when compared to the action of a deoxyribonucleoside kinase derived from human Herpes simplex preferably human Herpes simplex virus type 1 (HSV-1). One preferred example of such nucleoside analogues used for reference is gemcitabine (dFdC).

In a further aspect the invention relates to articles containing a nucleoside analogue and a plant deoxyribonucleoside kinase, or a gene coding for said plant deoxyribonucleoside kinase, or vector comprising said gene coding for said plant deoxyribonucleoside kinase, or a packaging cell line capable of producing an infective virion comprising said vector, as a combination for the simultaneous, separate or successive administration in cancer therapy.

Preferably, said plant deoxyribonucleoside kinase is enzyme is selected from the group consisting of:
- a plant deoxyribonucleoside kinase enzyme derived from thale cress (*Arabidopsis thaliana*), loblolly pine (*Pinus taeda*), from tomato (*Lycopersicum esculentum*), from maize (*Zea mays*) or from rice (*Oryza sativa*),
- a plant deoxyribonucleoside kinase enzyme comprising the amino acid sequence of SEQ ID NO: 2, SEQ ID NO: 4, SEQ ID NO: 6, SEQ ID NO: 8, SEQ ID NO: 10, or SEQ ID NO: 12,
- a plant deoxyribonucleoside kinase enzyme comprising an amino acid sequence of at least 70% identity with any one of said SEQ ID NOs, when determined over its entire length,
- a plant deoxyribonucleoside kinase enzyme having an amino acid sequence which, when aligned with a sequence selected from those presented in Table 1, comprises 60% or more of the residues identified in Table 1 as conserved residues, and
- a plant deoxyribonucleoside kinase as defined above having a C-terminal and/or N-terminal deletion in the order of 1-80 amino acid residues.

Such articles can be used in particular in the treatment of cancer.

Preferably the nucleoside analogue contained in said articles is selected from the group consisting of cytidine, adenosine and guanosine analogs. These nucleoside analogues can all be converted by the kinases described in the present invention, and provide a high therapeutic efficiency. More preferably the nucleoside analog is Gemcitabine.

In a further aspect the invention relates to a method of inhibiting a pathogenic agent in a warm-blooded animal, which method comprises administering to said animal a polynucleotide or a vector encoding a plant deoxyribonucleoside kinase enzyme, or a packaging cell line capable of producing an infective virion comprising said vector.

Preferably, the encoded plant deoxyribonucleoside kinase enzyme is selected from the group consisting of:
- a plant deoxyribonucleoside kinase enzyme derived from thale cress (*Arabidopsis thaliana*), loblolly pine (*Pinus taeda*), from tomato (*Lycopersicum esculentum*), from maize (*Zea mays*) or from rice (*Oryza sativa*),
- a plant deoxyribonucleoside kinase enzyme comprising the amino acid sequence of SEQ ID NO: 2, SEQ ID NO: 4, SEQ ID NO: 6, SEQ ID NO: 8, SEQ ID NO: 10, or SEQ ID NO: 12,
- a plant deoxyribonucleoside kinase enzyme comprising an amino acid sequence of at least 70% identity with any one of said SEQ ID NOs, when determined over its entire length,
- a plant deoxyribonucleoside kinase enzyme having an amino acid sequence which, when aligned with a sequence selected from those presented in Table 1, comprises 60% or more of the residues identified in Table 1 as conserved residues, and
- a plant deoxyribonucleoside kinase as defined in any of items ii or iii having a C-terminal and/or N-terminal deletion in the order of 1-80 amino acid residues.

Due to the improved and hitherto unknown kinetic properties of the enzymes described above these are particularly useful in treating said pathogenic agents.

According to the most preferred embodiment of the medical, pharmaceutical, and therapeutic aspects of the invention, the plant deoxyribonucleoside kinase is derived from thale cress (*Arabidopsis thaliana*), and the enzyme shows at least 80%, preferably at least 85%, more preferred at least 90%, most preferred at least 95% identity with the amino acid sequence presented as SEQ ID NO: 2.

In another aspect the invention provides plant deoxyribonucleoside linase enzymes derived from loblolly pine (*Pinus taeda*), from tomato (*Lycopersicum esculentum*), from maize (*Zea mays*) or from rice (*Oryza sativa*), as well as the nucleotide sequences coding for said plant deoxyribonucleoside kinases, vector constructs comprising said polynucleotide sequences and a promoter operably linked to the polynucleotide, packaging cell lines capable of producing infective virions, which cell lines comprises said expression vector of the invention, isolated host cells transduced/transfected/transformed with the expression vector of the invention.

The dCK/dGK like kinase enzymes from these four plant species constitute enzymes provided for the first time in purified form by the present invention. Due to the unexpected broad substrate specificity and the ability to phosphorylate a broad range of nucleoside analogues the kinases can be used for a wide range of applications, including medical use.

In a further aspect the invention relates to the use of the plant deoxyribonucleoside kinase enzyme of the invention for phosphorylation of nucleosides or nucleoside analogs.

In a still further aspect the invention provides methods of phosphorylating nucleosides or nucleoside analogs, comprising the steps of subjecting the nucleosides or nucleoside analogs to the action of the plant deoxyribonucleoside kinase enzyme of the invention, and recovering the phosphorylated nucleosides or nucleoside analogs.

This use and the corresponding method stems from the broad substrate specificity and/or the improved kinetic properties of the enzymes provided with the present invention.

In a further aspect the invention provides a method of non-invasive nuclear imaging of transgene expression of a plant deoxyribonucleoside kinase enzyme of the invention in a cell or subject.

For the development of effective clinical suicide gene therapy protocols, a non-invasive method to assay the extent, the kinetics and the spatial distribution of transgene expression is essential. Such imaging methods allow investigators and physicians to assess the efficiency of experimental and therapeutic gene transfection protocols and would enable early prognosis of therapy outcome.

Radionuclide imaging techniques like single photon emission computed tomography (SPECT) and positron emission tomography (PET), which can non-invasively visualize and quantify metabolic processes in vivo, are being evaluated for repetitive monitoring of transgene expression in living animals and humans. Transgene expression can be monitored directly by imaging the expression of the therapeutic gene itself, or indirectly using a reporter gene that is coupled to the therapeutic gene. Various radiopharmaceuticals have been developed and are now being evaluated for imaging of transgene expression.

In a further aspect the invention relates to a method of controlling or modifying growth of a plant, which plant comprises plant cells comprising a polynucleotide encoding a plant deoxyribonucleoside kinase enzyme of the invention which method comprises the step of exposing the plant or plant cells to a nucleoside analogue. Preferably said nucleoside analogue is gemcitabine.

Other objects of the invention will be apparent to the person skilled in the art from the following detailed description and examples.

DETAILED DISCLOSURE OF THE INVENTION

Pharmaceutical Compositions

In one aspect the invention relates to a pharmaceutical composition comprising a therapeutically effective amount of at least one plant deoxyribonucleoside kinase enzyme, or a polynucleotide sequence encoding said at least one plant deoxyribonucleoside kinase enzyme, or an expression vector comprising said polynucleotide sequence, or a packaging cell line capable of producing an infective virion comprising said vector, or an isolated host cell transduced with the vector, and a pharmaceutically acceptable carrier or diluent.

Preferably the plant deoxyribonucleoside kinase enzyme is selected from the group consisting of:

- a plant deoxyribonucleoside kinase enzyme derived from thale cress (*Arabidopsis thaliana*), loblolly pine (*Pinus taeda*), from tomato (*Lycopersicum esculentum*), from maize (*Zea mays*)or from rice (*Oryza sativa*),
- a plant deoxyribonucleoside kinase enzyme comprising the amino acid sequence of SEQ ID NO: 2, SEQ ID NO: 4, SEQ ID NO: 6, SEQ ID NO: 8, SEQ ID NO: 10, or SEQ ID NO: 12,
- a plant deoxyribonucleoside kinase enzyme comprising an amino acid sequence of at least 70% identity with any one of said SEQ ID Nos, when determined over its entire length,
- a plant deoxyribonucleoside kinase enzyme having an amino acid sequence which, when aligned with a sequence selected from those presented in Table 1, comprises 60% or more of the residues identified in Table 1 as conserved residues, and
- a plant deoxyribonucleoside kinase as defined above having a C-terminal and/or N-terminal deletion in the order of 1-80 amino acid residues.

In some embodiments the pharmaceutical composition comprises a gene coding for the deoxyribonucleoside kinase, an expression vector comprising said gene or a packaging cell line capable of producing an infective virion comprising said vector. For these embodiments, the preferred polynucleotide sequence comprising the sequence coding for the deoxyribonucleoside kinase is selected from the group consisting of:

- the polynucleotide sequence of any of SEQ ID No 1, 3, 5, 7, 9, or 11;
- a polynucleotide sequence having at least 70% sequence identity with any of SEQ ID No 1, 3, 5, 7, 9, or 11 when determined over its entire length;
- a polynucleotide sequence capable of hybridising under at least medium stringency conditions with a polynucleotide sequence presented as SEQ ID No 1, 3, 5, 7, 9, or 11; and
- a functional analog of any of SEQ ID No 1, 3, 5, 7, 9, or 11.

For the medical, pharmaceutical and therapeutic aspects of the invention, the preferred plant deoxyribonucleoside kinase enzymes are selected from the group consisting of:

- a plant deoxyribonucleoside kinase enzyme derived from thale cress (*Arabidopsis thaliana*), from tomato (*Lycopersicum esculentum*),
- a plant deoxyribonucleoside kinase enzyme comprising the amino acid sequence of SEQ ID NO: 2, SEQ ID NO: 6,
- a plant deoxyribonucleoside kinase enzyme comprising an amino acid sequence of at least 80% identity with any one said SEQ ID Nos, when determined over its entire length, and
- a plant deoxyribonucleoside kinase as defined above having an N-terminal or C-terminal deletion in the order of 1-80 amino acid residues.

These enzymes have improved kinetic properties and broader substrate specifictity compared to known dNKs, in particular compared to a deoxyribonucleoside kinase derived from human Herpes simplex, in particular human Herpes simplex virus type 1 (HSV-1).

In terms of polynucleotide sequences encoding a plant deoxyribonucleoside kinase enzyme the corresponding preferred sequences are selected from the group consisiting of:

- a polynucleotide sequence represented by SEQ ID No 1 or 5;
- a polynucleotide sequence having at least 80% sequence identity with SEQ ID No 1 or 5 when determined over its entire length;
- a polynucleotide sequence derived from SEQ ID No 1 or 5 having a 5' and/or 3' deletion in the order of 3 to 240 nucleotides.

More preferably the enzymes for the medical, pharmaceutical and therapeutic aspects are derived from thale cress (*Arabidopsis thaliana*), and which enzyme shows at least 80%, preferably at least 85%, more preferred at least 90%, most preferred at least 95% identity with the amino acid sequence presented as SEQ ID NO: 2. In the assays provided in the examples, the dNK from thale cress was most efficient in phosphorylating both deoxyribonucleosides and analogs.

In terms of polynucleotide sequences this corresponds to the plant deoxyribonucleoside kinase encoding sequence derived from thale cress (*Arabidopsis thaliana*), which sequence shows at least 80%, preferably at least 85%, more preferred at least 90%, most preferred at least 95% identity with the polynucleotide sequence presented as SEQ ID No. 1.

For use in therapy the plant deoxyribonucleoside kinase enzyme of the invention may be administered in any convenient form. In a preferred embodiment, plant deoxyribonucleoside kinase enzyme of the invention is incorporated into a pharmaceutical composition together with one or more adjuvants, excipients, carriers and/or diluents, and the pharmaceutical composition prepared by the skilled person using conventional methods known in the art.

The composition may be administered alone or in combination with one or more other agents, drugs or hormones.

The pharmaceutical composition of this invention may be administered by any suitable route, including, but not limited to oral, intravenous, intramuscular, interarterial, intramedullary, intrathecal, intraventricular, transdermal, subcutaneous, intraperitoneal, intranasal, anteral, topical, sublingual or rectal application, buccal, vaginal, intraorbital, intracerebral, intracranial, intraspinal, intraventricular, intracisternal, intracapsular, intrapulmonary, transmucosal, or via inhalation.

Further details on techniques for formulation and administration may be found in the latest edition of *Remington's Pharmaceutical Sciences* (Maack Publishing Co., Easton, Pa.).

The active ingredient may be administered in one or several doses per day. Currently contemplated appropriate dosages are between 0.5 ng to about 50 µg/kg deoxyribonucleoside kinase/kg body weight per administration, and from about 1.0 ng/kg to about 100 µg/kg daily.

The dose administered must of course be carefully adjusted to the age, weight and condition of the individual being treated, as well as the route of administration, dosage form and regimen, and the result desired, and the exact dosage should of course be determined by the practitioner.

In further embodiments, the plant deoxyribonucleoside kinase of the invention may be administered by genetic delivery, using cell lines and vectors as described below under methods of treatment.

Therefore, in another preferred embodiment, the invention provides pharmaceutical compositions comprising the polynucleotide of the invention, or a vector of the invention, or a packaging cell of the invention, or a host cell of the invention, and a pharmaceutically acceptable carrier or diluent.

To generate such therapeutic cell lines, the polynucleotide of the invention may be inserted into an expression vector, e.g. a plasmid, virus or other expression vehicle, and operatively linked to expression control sequences by ligation in a way that expression of the coding sequence is achieved under conditions compatible with the expression control sequences.

Suitable expression control sequences include promoters, enhancers, transcription terminators, start codons, splicing signals for introns, and stop codons, all maintained in the correct reading frame of the polynucleotide of the invention so as to permit proper translation of mRNA. Expression control sequences may also include additional components such as leader sequences and fusion partner sequences.

Methods of Treatment

The present invention, which relates to polynucleotides and proteins, polypeptides, or derivatives produced therefrom, may be used for treating or alleviating a disorder or disease of a living animal body, including a human, which disorder or disease is responsive to the activity of a cytotoxic agent.

The disorder, disease or condition may in particular be a cancer or a viral infection.

The polynucleotides of the present invention may in particular be used as a "suicide gene", i.e. a drug-susceptibility gene. Transfer of a suicide gene to a target cell renders the cell sensitive to compounds or compositions that are relatively non-toxic to normal cells.

Therefore, in one aspect, the invention provides a method for sensitising target cells to prodrugs, which method comprises the steps of
 (i) transfecting the target cell with a polynucleotide sequence encoding a plant deoxyribonucleoside kinase enzyme that promotes the conversion of said prodrug into a (cytotoxic) drug; and
 (ii) delivering said prodrug to said target cell;
wherein said target cell is more sensitive to said (cytotoxic) drug than to aid prodrug.

In its broadest aspect any plant deoxyribonucleoside kinase enzyme may be used. However, more preferably the encoded plant deoxyribonucleoside kinase enzyme is selected from the group consisting of:
 a plant deoxyribonucleoside kinase enzyme derived from thale cress *Arabidopsis thaliana*, loblolly pine (*Pinus taeda*), from tomato (*Lycopersicum esculentum*), from maize (*Zea mays*)or from rice (*Oryza sativa*),
 a plant deoxyribonucleoside kinase enzyme comprising the amino acid sequence of SEQ ID NO: 2, SEQ ID NO: 4, SEQ ID NO: 6, SEQ ID NO: 8, SEQ ID NO: 10, or SEQ ID NO: 12,
 a plant deoxyribonucleoside kinase enzyme comprising an amino acid sequence of at least 70% identity with any one of said SEQ ID Nos, when determined over its entire length,
 a plant deoxyribonucleoside kinase enzyme having an amino acid sequence which, when aligned with a sequence selected from those presented in Table 1, comprises 60% or more of the residues identified in Table 1 as conserved residues, and
 a plant deoxyribonucleoside kinase as defined above having a C-terminal and/or N-terminal deletion in the order of 1-80 amino acid residues.

For the therapeutic aspects of the invention, the preferred plant deoxyribonucleoside kinase enzymes are selected from the group consisting of:
 a plant deoxyribonucleoside kinase enzyme derived from thale cress (*Arabidopsis thaliana*), from tomato (*Lycopersicum esculentum*),
 a plant deoxyribonucleoside kinase enzyme comprising the amino acid sequence of SEQ ID NO: 2, SEQ ID NO: 6,
 a plant deoxyribonucleoside kinase enzyme comprising an amino acid sequence of at least 80% identity with any one said SEQ ID Nos, when determined over its entire length, and
 a plant deoxyribonucleoside kinase as defined above having an N-terminal or C-terminal deletion in the order of 1-80 amino acid residues.

These enzymes have improved kinetic properties and broader substrate specifictity compared to known dNKs, in particular compared to a deoxyribonucleoside kinase derived from human Herpes simplex, in particular human Herpes simplex virus type 1 (HSV-1).

More preferably the enzymes for the medical, pharmaceutical and therapeutic aspects are derived from thale cress (*Arabidopsis thaliana*), and which enzyme shows at least 80%, preferably at least 85%, more preferred at least 90%, most preferred at least 95% identity with the amino acid sequence presented as SEQ ID NO: 2. In the assays provided in the examples, the dNK from thale cress was most efficient in phosphorylating both deoxyribonucleosides and analogs.

The deoxyribonucleoside kinase enzyme invention may be used directly via e.g., injected, implanted or ingested pharmaceutical compositions to treat a pathological process responsive to the deoxyribonucleoside kinase enzyme.

The polynucleotide of the invention, including the complementary sequences thereof, may be used for the expression of the deoxyribonucleoside kinase enzyme of the invention. This may be achieved by cell lines expressing such proteins, peptides or derivatives of the invention, or by virus vectors encoding such proteins, peptides or derivatives of the invention, or by host cells expressing such proteins, peptides or derivatives. These cells, vectors and compositions may be administered to treatment target areas to affect a disease process responsive to cytotoxic agents.

Suitable expression vectors may be a viral vector derived from Herpes simplex, adenovira, lentivira, retrovira, or vaccinia vira, or from various bacterially produced plasmids, and may be used for in vivo delivery of nucleotide sequences to a whole organism or a target organ, tissue or cell population. Other methods include, but are not limited to, liposome transfection, electroporation, transfection with carrier peptides containing nuclear or other localising signals, and gene delivery via slow-release systems. In still another aspect of the invention, "antisense" nucleotide sequences complementary to the nucleotide of the invention or portions thereof, may be used to inhibit or enhance deoxyribonucleoside kinase enzyme expression.

In another preferred embodiment the invention provides methods for inhibiting pathogenic agents in warm-blooded animals, which methods comprises the step of administering to said animal a polynucleotide of the invention, or an expression vector of the invention.

In a more preferred embodiment the polynucleotide sequence or the expression vector is administered in vivo.

In another preferred embodiment the pathogenic agent is a virus, a bacteria or a parasite, or even a tumour cell.

In another preferred embodiment the pathogenic agent is an autoreactive immune cell.

In an even more preferred embodiment the method further comprises the step of administering a nucleoside analogue to said warm-blooded animal.

Prodrugs/Nucleoside Analogs

Numerous nucleoside analogs exist that can be converted into a toxic product by the dNKs described in the present invention.

In a preferred embodiment the prodrug is a nucleoside analogue. Nucleoside analogues that are suitable for use according to the invention include aciclovir (9-[2-hydroxyethoxy]-methyl-guanosine), buciclovir, famciclovir, ganciclovir (9-[2-hydroxy-1-(hydroxymethyl)ethoxyl-methyl]-guanosine), penciclovir, valciclovir, trifluorothymidine, AZT (3'-azido-3'-thymidine), AIU (5'-iodo-5'-amino-2',5'-dideoxyuridine), ara-A (adenosine-arabinoside; Vivarabine), ara-C (cytidine-arabinoside), ara-G (9-beta-D-arabinofuranosylguanine), ara-T, 1-beta-D-arabinofuranosyl thymine, 5-ethyl-2'-deoxyuridine, 5-iodo-5'-amino-2,5'-dideoxyuridine, 1-[2-deoxy-2-fluoro-beta-D-arabino furanosyl]-5-iodouracil, idoxuridine (5-iodo-2'deoxyuridine), fludarabine (2-Fluoroadenine 9-beta-D-Arabinofuranoside), gencitabine, 3'-deoxyadenosine (3-dA), 2',3'-dideoxyinosine (ddI), 2',3'-dideoxycytidine (ddC), 2',3'-dideoxythymidine (ddT), 2',3'-dideoxyadenosine (ddA), 2',3'-dideoxyguanosine (ddG), 2-chloro-2'-deoxyadenosine (2CdA), 5-fluorodeoxyuridine, BVaraU ((E)-5-(2-bromovinyl)-1-beta-D-arabinofuranosyluracil), BVDU (5-bromovinyl-deoxyuridine), FIAU (1-(2-deoxy-2-fluoro-beta-D-arabinofuranosyl)-5-iodouracil), 3TC (2'-deoxy-3'-thiacytidine), dFdC gemcitabine (2',2'-difluorodeoxycytidine), dFdG (2',2'-difluorodeoxyguanosine), 5-fluorodeoxyuridine (FdUrd), d4T (2',3'didehydro-3'-deoxythymidine), ara-M (6-methoxy purinearabinonucleoside), IudR (5-Jodo-2'deoxyuridine), CaFdA (2-chloro-2-ara-fluoro-deoxyadenosine), ara-U (1-beta-D-arabinofuranosyluracil), FBVAU (E)-5-(2-bromovinyl)-1-(2-deoxy-2-fluoro-beta-D-arabinofuranosyl)uracil), FMAU 1-(2-deoxzy-2-fluoro-beta-D-arabinofuranosyl)-5-methyluracil, FLT 3'-fluoro-2'-deoxythymidine, 5-Br-dUrd 5-bromodeoxyuridine, 5-Cl-dUrd 5-chlorodeoxyuridine, dFdU 2',2'-difluorodeoxyuridine, (−)Carbovir (C-D4G), 2,6-Diamino-ddP (ddDAPR; DAPDDR; 2,6-Diamino-2',3'-dideoxypurine-9-ribofuranoside), 9-(2'-Azido-2',3'-dideoxy-β-D-erythropentofuranosyl)adenine (2'-Azido-2',3'-dideoxyadenosine; 2'-N3ddA), 2'FddT (2'-Fluoro-2',3'-dideoxy-β-D-erythro-pentofuranosyl)thymine), 2'-N3ddA (β-D-threo) (9-(2'-Azido-2',3'-dideoxy-β-D-threopentofuranosyl)adenine), 3-(3-Oxo-1-propenyl)AZT (3-(3-Oxo-1-propenyl)-3'-azido-3'-deoxythymidine), 3'-Az-5-Cl-ddC (3'-Azido-2',3'-dideoxy-5-chlorocytidine), 3'-N3-3'-dT (3'-Azido-3'-deoxy-6-azathymidine), 3'-F4Thio-ddT (2',3'-Dideoxy-3'-fluoro-4-thiothymidine), 3'-F-5-Cl-ddC (2',3'-Dideoxy-3'-fluoro-5-chlorocytidine), 3'-FddA (B-D-Erythro) (9-(3'-Fluoro-2',3'-dideoxy-B-D-erythropentafuranosyl)adenine), Uravidine (3'-Azido-2',3'-dideoxyuridine; AzdU), 3'-FddC (3'-Fluoro-2',3'-dideoxycytidine), 3'-FddDAPR (2,6-Diaminopurine-3'-fluoro-2',3'-dideoxyriboside), 3'-FddG (3'-Fluoro-2',3'-dideoxyguanosine), 3'-FddU (3'-Fluoro-2',3'-dideoxyuridine), 3'-Hydroxymethyl-ddC (2',3'-Dideoxy-3'-hydroxymethyl cytidine; BEA-005), 3'-N3-5-CF3-ddU (3'-Azido-2',3'-dideoxy-5-trifluoromethyluridine), 3'-N3-5-Cyanomethyloxy-ddU (3'-Azido-2',3'-dideoxy-5-[(cyanomethyl)oxy]uridine), 3'-N3-5-F-ddC (3'-Azido-2',3'-dideoxy-5-fluorocytidine), 3'-N3-5-Me-ddC (CS-92; 3'-Azido-2',3'-dideoxy-5-methylcytidine), 3'-N3-5-NH2-ddU (3'-Azido-2',3'-dideoxy-5-aminouridine), 3'-N3-5-NHMe-ddU (3'-Azido-2',3'-dideoxy-5-methyaminouridine), 3'-N3-5-NMe2-ddU (3'-Azido-2',3'-dideoxy-5-dimethylaminouridine), 3'-N3-5-OH-ddU (3'-Azido-2',3'-dideoxy-5-hydroxyuridine), 3'-N3-5-SCN-ddU (3'-Azido-2',3'-dideoxy-5-thiocyanatouridine), 3'-N3-ddA (9-(3'-Azido-2',3'-dideoxy-B-D-erythropentafuranosyl)adenine), 3'-N3-ddC (CS-91; 3'-Azido-2',3'-dideoxycytidine), 3'-N3ddG (AZG; 3'-Azido-2',3'-dideoxyguanosine), 3'-N3-N4-5-diMe-ddC (3'-Azido-2',3'-dideoxy-N4-5-dimethylcytidine), 3'-N3-N4-OH-5-Me-ddC (3'-Azido-2',3'-dideoxy-N4-OH-5-methylcytidine), 4'-Az-3'-dT (4'-Azido-3'-deoxythymidine), 4'-Az-5CldU (4'-Azido-5chloro-2'-deoxyuridine), 4'-AzdA (4'-Azido-2'-deoxyadenosine), 4'-AzdC (4'-Azido-2'-deoxycytidine), 4'-AzdG (4'-Azido-2'-deoxyguanosine), 4'-AzdI (4'-Azido-2'-deoxyinosine), 4'-AzdU (4'-Azido-2'-deoxyuridine), 4'-Azidothymidine (4'-Azido-2'-deoxy-.beta.-D-erythropentofuranosyl-5-methyl-2,4-dioxopyrimidine), 4'-CN-T (4'-Cyanothymidine), 5-Et-ddC (2',3'-Dideoxy-5-ethylcytidine), 5-F-ddC (5-Fluoro-2',3'-dideoxycytidine), 6Cl-ddP (D2ClP; 6-Chloro-ddP; CPDDR; 6-Chloro-9-(2,3-dideoxy-.beta.-D-glyceropentofuranosyl)-9H-purine), 935U83 (2',3'-Dideoxy-3'-fluoro-5-chlorouridine; 5-Chloro-2',3'-dideoxy-3'-fluorouridine; FddClU; Raluridine), AZddBrU (3'-N3-5-Br-ddU; 3'-Azido-2',3'-dideoxy-5-bromouridine), AzddClU; AzddClUrd (3'-Azido-5-chloro-2',3'-dideoxyuridine), AZddEtU (3'-N3-5-EtddU; CS-85; 3'-Azido-2',3'-dideoxy-5-ethyluridine), AZddFU (3'-Azido-2',3'-dideoxy-5-fluorouridine), AZddIU (3'-N3-5-I-ddU; 3'-Azido-2',3'-dideoxy-5-iodouridine), AZT-2,5'-anhydro (2,5'-Anhydro-3'-azido-3'-deoxythymidine), AZT-α-L (α-L-AZT), AZU-2,5'-anhydro (2,5'-Anhydro-3'-azido-2',3'-dideoxyuridine), C-analog of 3'-N3-ddU (3'-Azido-2',3'-dideoxy-5-aza-6-deazauridine), D2SMeP (9-(2,3-Dideoxy-β-D-ribofuranosyl)-6-(methylthio)purine), D4A (2',3'-Dideoxydidehydroadenosine), D4C (2',3'-Didehydro-3'-deoxycytidine), D4DAP (2,6-Diaminopurine-2',3'-dideoxydidehydroriboside; ddeDAPR), D4FC (D-D4FC; 2',3'-Didehydro-2',3'-dideoxy-5-fluorocytidine), D4G (2',3'-Didehydro-2',3'-dideoxyguanosine), DMAPDDR (N-6-dimethyl ddA; 6-Dimethylaminopurine-2',3'-dideoxyriboside), dOTC (−) ((−)-2'-Deoxy-3'-oxa-4'-thiocytidine), dOTC (+) ((+)-2'-Deoxy-3'-oxa-4'-thiocytidine), dOTFC (−) ((−)-2'-Deoxy-3'-oxa-4'-thio-5-fluorocytidine), dOTFC (+) ((+)-2'-Deoxy-3'-oxa-4'-thio-5-fluorocytidine), DXG ((−)-β-Dioxolane-G), DXC-α-L-(α-L-Dioxalane-C), FddBrU (2',3'-Dideoxy-3'-fluoro-5-bromouridine), FddIU (3'-Fluoro-2',3'-dideoxy-5-iodouridine), FddT (Alovudine; 3'-FddT; FddThD; 3'-FLT; FLT), FTC (Emtricitabine; Coviracil; (−)-FTC; (−)-2',3'-Dideoxy-5-fluoro-3'-thiacytidine), FTC-α-L-(α-L-FTC), L-D4A (L-2',3'-Didehydro-2',3'-dideoxyadenosine), L-D4FC (L-2',3'-Didehydro-2',3'-dideoxy-5-fluorocytidine), L-D4I (L-2',3'-Didehydro-2',3'-dideoxyinosine), L-D4G (L-2',3'-Didehydro-2',3'-deoxyguanosine), L-FddC (β-L-5F-ddC), Lodenosine (F-ddA; 2'-FddA (B-D-threo); 2'-F-ddara-A; 9-(2'-Fluoro-2',3'-dideoxy-B-D-threopentafuranosyl) adenine), MeAZddIsoC (5-Methyl-3'-azido-2',3'-dideoxyisocytidine), N6-Et-ddA (N-Ethyl-2',3'-dideoxyadenosine), N-6-methyl ddA (N6-Methyl-2',3'-dideoxyadenosine) or RO31-6840 (1-(2',3'-Dideoxy-2'-fluoro-β-D-threo-pentofuranosyl)cytosine).

More preferably the nucleoside analog is cytidine analog, a guanosine analog or an adenosine analog. Preferred examples of such cytidine, guanosine and adenosine analogs include dFdC gemcitabine (2',2'-difluorodeoxycytidine), 2-chloro-2'-deoxyadenosine (2CdA), CaFdA (2-chloro-2-ara-fluoro-deoxyadenosine), fludarabine (2-Fluoroadenine 9-beta-D-Arabinofuranoside), 2',3'-dideoxycytidine (ddC), 2',3'-dideoxyadenosine (ddA), 2',3'-dideoxyguanosine (ddG), ara-A (adenosine-arabinoside; Vivarabine), ara-C (cytidine-arabinoside), ara-G (9-beta-D-arabinofuranosylguanine), aciclovir (9-[2-hydroxy-ethoxy]-methyl-guanosine), buciclovir, famciclovir, ganciclovir (9-[2-hydroxy-1-(hydroxymethyl)ethoxyl-methyl]-guanosine), penciclovir, valciclovir, 3TC (2'-deoxy-3'-thiacytidine), dFdG (2',2'-difluorodeoxyguanosine), 2,6-Diamino-ddP (ddDAPR; DAPDDR; 2,6-Diamino-2',3'-dideoxypurine-9-ribofuranoside), 9-(2'-Azido-2',3'-dideoxy-β-D-erythropentofuranosyl)adenine (2'-Azido-2',3'-dideoxyadenosine; 2'-N3ddA), 2'-N3ddA(β-D-threo) (9-(2'-Azido-2',3'-dideoxy-β-D-threopentofuranosyl)adenine), 3'-Az-5-Cl-ddC (3'-Azido-2',3'-dideoxy-5-chlorocytidine), 3'-F-5-Cl-ddC (2',3'-Dideoxy-3'-fluoro-5-chlorocytidine), 3'-FddA (B-D-Erythro) (9-(3'-Fluoro-2',3'-dideoxy-B-D-erythropentafuranosyl)adenine), 3'-FddC (3'-Fluoro-2',3'-dideoxycytidine), 3'-F-ddDAPR (2,6-Diaminopurine-3'-fluoro-2',3'-dideoxyriboside), 3'-FddG (3'-Fluoro-2',3'-dideoxyguanosine), 3'-Hydroxymethyl-ddC (2',3'-Dideoxy-3'-hydroxymethyl cytidine; BEA-005), 3'-N3-5-F-ddC (3'-Azido-2',3'-dideoxy-5-fluorocytidine), 3'-N3-5-Me-ddC (CS-92; 3'-Azido-2',3'-dideoxy-5-methylcytidine), 3'-N3-ddA (9-(3'-Azido-2',3'-dideoxy-B-D-erythropentafuranosyl)adenine), 3'-N3-ddC (CS-91; 3'-Azido-2',3'-dideoxycytidine), 3'-N3ddG (AZG; 3'-Azido-2',3'-dideoxyguanosine), 3'-N3-N4-5-diMe-ddC (3'-Azido-2',3'-dideoxy-N4-5-dimethylcytidine), 3'-N3-N4-OH-5-Me-ddC (3'-Azido-2',3'-dideoxy-N4-OH-5-methylcytidine), 4'-AzdA (4'-Azido-2'-deoxyadenosine), 4'-AzdC (4'-Azido-2'-deoxycytidine), 4'-AzdG (4'-Azido-2'-deoxyguanosine), 5-Et-ddC (2',3'-Dideoxy-5ethylcytidine), 5-F-ddC (5-Fluoro-2',3'-dideoxycytidine), 6Cl-ddP (D2ClP; 6-Chloro-ddP; CPDDR; 6-Chloro-9-(2,3-dideoxy-.beta.-D-glyceropentofuranosyl)-9H-purine), D2SMeP (9-(2,3-Dideoxy-β-D-ribofuranosyl)-6-(methylthio)purine), D4A (2',3'-Dideoxydidehydroadenosine), D4C (2',3'-Didehydro-3'-deoxycytidine), D4DAP (2,6-Diaminopurine-2',3'-dideoxydidehydroriboside; ddeDAPR), D4FC (D-D4FC; 2',3'-Didehydro-2',3'-dideoxy-5-fluorocytidine), D4G (2',3'-Didehydro-2',3'-dideoxyguanosine), DMAPDDR (N-6-dimethyl ddA; 6-Dimethylaminopurine-2',3'-dideoxyriboside), dOTC (−) ((−)-2'-Deoxy-3'-oxa-4'-thiocytidine), dOTC (+) ((+)-2'-Deoxy-3'-oxa-4'-thiocytidine), dOTFC (−) ((−)-2'-Deoxy-3'-oxa-4'-thio-5-fluorocytidine), dOTFC (+) ((+)-2'-Deoxy-3'-oxa-4'-thio-5-fluorocytidine), DXG ((−)-β-Dioxolane-G), DXC-α-L-(α-L-Dioxalane-C), FTC (Emtricitabine; Coviracil; (−)-FTC; (−)-2',3'-Dideoxy-5-fluoro-3'-thiacytidine), FTC-α-L-(α-L-FTC), L-D4A (L-2',3'-Didehydro-2',3'-dideoxyadenosine), L-D4FC (L-2',3'-Didehydro-2',3'-dideoxy-5-fluorocytidine), L-D4I (L-2',3'-Didehydro-2',3'-dideoxyinosine), L-D4G (L-2',3'-Didehydro-2',3'-deoxyguanosine), L-FddC (β-L-5F-ddC), Lodenosine (F-ddA; 2'-FddA (B-D-threo); 2'-F-ddara-A; 9-(2'-Fluoro-2',3'-dideoxy-B-D-threopentafuranosyl) adenine), MeAZddIsoC (5-Methyl-3'-azido-2',3'-dideoxyisocytidine), N6-Et-ddA (N-Ethyl-2',3'-dideoxyadenosine), N-6-methyl ddA (N6-Methyl-2',3'-dideoxyadenosine) or RO31-6840 (1-(2',3'-Dideoxy-2'-fluoro-β-D-threo-pentofuranosyl)cytosine).

In a especially preferred embodiment the nucleoside analog is Gemcitabine which is shown in the examples to be converted effectively by the enzymes of the present invention into a toxic product.

Plant Deoxyribonucleoside Kinase Enzymes

The invention relates to plant dCK/dGK-like deoxyribonucleoside kinase enzymes. By a dCK/dGK-like deoxyribonucleoside kinase enzyme is understood an enzyme which can phosphorylate at least dAdo, dGuo, and dCyd as shown in Example 3. This does not exclude that the kinases have activity towards other deoxyribonucleosides as can be seen in the examples.

In one embodiment, the plant dCK/dGK-like deoxyribonucleoside kinase enzymes, upon transducton into a cell, decreases at least 3 fold the lethal dose ($LD_{100}$) of at least one nucleoside analogue when compared to the action of a deoxyribonucleoside kinase derived from human Herpes simplex, in particular human Herpes simplex virus type 1 (HSV-1). Preferably said at least one nucleoside analogue is Gemcitabine.

In one aspect, the plant dCK/dGK-like deoxyribonucleoside kinase of the invention is derived from thale cress *Arabidopsis thaliana*, from loblolly pine (*Pinus taeda*), from tomato (*Lycopersicum esculentum*), from maize (*Zea mays*) or from rice (*Oryza sativa*).

For the medical, pharmaceutical and therapeutic aspects of the invention, the most preferred plant deoxyribonucleoside kinase enzymes are selected from the group consisting of:

a plant deoxyribonucleoside kinase enzyme derived from thale cress (*Arabidopsis thaliana*), from tomato (*Lycopersicum esculentum*), a plant deoxyribonucleoside kinase enzyme comprising the amino acid sequence of SEQ ID NO: 2, SEQ ID NO: 6, a plant deoxyribonucleoside kinase enzyme comprising an amino acid sequence of at least 70% identity with any one said SEQ ID Nos, when determined over its entire length, and a plant deoxyribonucleoside kinase as defined above having an N-terminal or C-terminal deletion in the order of 180 amino acid residues.

These enzymes have improved kinetic properties and broader substrate specifictity compared to known dNKs, in particular compared to a deoxyribonucleoside kinase derived from human Herpes simplex, in particular human Herpes simplex virus type 1 (HSV-1).

More preferably the enzymes for the medical, pharmaceutical and therapeutic aspects are derived from thale cress (*Arabidopsis thaliana*), and which enzyme shows at least 80%, preferably at least 85%, more preferred at least 90%, most preferred at least 95% identity with the amino acid sequence presented as SEQ ID NO: 2. In the assays provided in the examples, the dNK from thale cress was most efficient in phosphorylating both deoxyribonucleosides and analogs.

In one embodiment, the plant deoxyribonucleoside kinases of the invention are multi-substrate kinases, capable of converting all four natural deoxyribonucleosides (dThd, dCyd, dAdo, dGuo). This can in particular be obtained by C- and/or N-terminal deletions.

In another embodiment, the invention provides isolated plant deoxyribonucleoside kinase enzymes (dNK) derived from loblolly pine (*Pinus taeda*), from tomato (*Lycopersicum esculentum*), from maize (*Zea mays*) and from rice (*Oryza sativa*). More specifically the isolated plant deoxyribonucleoside kinase enzymes of the invention are deoxycytidine kinases (dCK) and/or deoxyguanosine kinases (dGK), herein designated as dCK/dGK-like kinases.

Based on a Clustal W (1.8) multiple amino acid sequence alignment of the loblolly pine, tomato, maize and rice deoxyribonucleoside kinases with a plant deoxyribonucleoside kinase derived from *Arabidopsis thaliana*, several conserved, semi-conserved and lesser-conserved residues were identified, as shown in Table 1 below.

TABLE 1

Clustal W (1.8) Multiple Amino Acid Sequence Alignment

```
AT-dCK/dGK       MVDYLRSSVGIIHRNHAESITTRIIKESVDDELKDSGPEPNLN--VKKRLTFCVEGNISVG   58
Tomato-dCK/dGK   MVEPLQSSIGIIHRNHAESITTYIRKSVDEELKNNSDSNVKSTQKKRLTFCVEGNISVG   60
Pine-dCK/dGK     ----------------------------------------------------NISVG    5
Maize-dCK/dGK    -----------------------------------------------------------
Rice-dCK/dGKII   MVEPLQSSVGIIHKNHAESITLFIKESVDEELKGTDSP---NVSKNKRLTFCVEGNISVG   57
Rice-dCK/dGKI    -----------------------------------------------------------
                 +++++++++++++++++++++++++++++++++++++++++++++++
                 %%::%:%%:%%%%:%%%%%%% :%: %%%:%%%    :     :   :%%%%%%%%%%%%

AT-dCK/dGK       KSTFLQRIANETVELQDLVEIVPEPVDKWQDYGPDHFNILDAFYSEPQRYAYTFQNYVFV  118
Tomato-dCK/dGK   KTTFLQRIANETVELQDLVEIVPEPIAKWQDKGPDHFNILDAFYAEPQRYAYTFQNYVFV  120
Pine-dCK/dGK     KTTFLQRIANETVELRDLVEVVPGPISKWQDRGPDHFNILDAFYAEPQRYAYTFQNYVFV   65
Maize-dCK/dGK    -----------------------------------FNVLDAFYAEPQRYAYTFQNYVFV   24
Rice-dCK/dGKII   KTTFLQRIANETVELRDLVEIVPEPIAKWQDKGPDHFNILDAFYAEPQRYAYTFQNYVFV  117
Rice-dCK/dGKI    -----------------------------------------------------------
                 %:%%%%%%%%%%%:%%:%%%%:%% %:  %%%%:%%%%%%%:%%%%%:%%%%%%%%%%%%

AT-dCK/dGK       TRLMQEKESASGVKPLRLMERSVFSDRMVFVRAVHEAKWMNEMEISIYDSWFDPVVSSLP  178
Tomato-dCK/dGK   TRVMQERESSGGIRPLRLMERSVFSDRMVFVRAVHEANWMNEMEISIYDSWFDPVVSTLP  180
Pine-dCK/dGK     TRVMQERESAGSLKPLRLMERSVFSDRMVFVRAVHEAKWMNGMELSIYDSWFDPVVSVLP  125
Maize-dCK/dGK    TRVMQEKESACGVKPLRLMERSVFSDRMVFVRAVHEANWMNEMEISIYDSWFDPVVSSLP   84
Rice-dCK/dGKII   TRVMQEKESSSGVKPLRLMERSVFSDRMVFVRAVHEANWMNEMEISIYDSWFDPVVSSLP  177
Rice-dCK/dGKI    -----------------------------------------------------------
                 %%:%%%%:%%:  :::%%%%%%%%%%%%%%%%%%%%%%%:%%% %%:%%%%%%%%%% %%

AT-dCK/dGK       GLVPDGFIYLRASPDTCHKRMMLRKRSEEGGVSLKYLQDLHEKHESWLLPEESGIHGVLS  238
Tomato-dCK/dGK   GLIPDGFIYLRASPDTCHKRMMLRKRSEEGGVSLEYLRGLHEKHESWLPPEESGNHGVLS  240
Pine-dCK/dGK     GLVPDGFIYLRASPDTCHRALQLRKREENSVSLDYLRGLHEKHENWLPPEEGSHGLLS   185
Maize-dCK/dGK    GLVPDGFIYLRASPDTCHKRMMVRKRSEEAGVILDYLRGLHEKHESWLLPSKGGESGVLS  144
Rice-dCK/dGKII   GLIPDGFIYLRASPDTCHKRMMVRKRSEEGGVILDYLRGLHEKHESWLLPSKGQSPGVLS  237
Rice-dCK/dGKI    -----------------------------------------------------------
                 %%:%%%%%%%%%%%%%%%:  : :%%% %% :%:% %%::%%%%%:%%:%     : %:%%

AT-dCK/dGK       VSREESLHMDNSLHPDIKDRVFYLEGNHMHSSIQKVPALVLDCEPNIDFSRDIEAKTQYAR  298
Tomato-dCK/dGK   VSELPLNSDKSVSPEIRDRVFYLEGNHMHSSIQKVPALVLDCEPNIDFNRDIEAKRQYAR  300
Pine-dCK/dGK     VSQLPLDSDRSLHPEIRDRTFLLQGDHVHSSIQKVPALVLDCEPNIDFSRDIEAKQGYAR  245
Maize-dCK/dGK    ESQLPVHMEGSLHADIRDRVFYLEGDHMHSSIQKVPALILDCEHHIDFNKDIEAKTQYAR  204
Rice-dCK/dGKII   VSQVPVHMEGSLPPDIRNRVFYLEGDHMHSSIQKVPALVLDCEHHIDFNKDIEAKTQYAR  297
Rice-dCK/dGKI    ---------------------------------------------------QYAQ      4
                 :%:  :::   :  %:  ::%:%:%  % %:%:%:%:%%%%%%%%:%%%%  :%%%::%%%%%  %%:

AT-dCK/dGK       QVAEFFEFVKKKQETST-------EKSNSQSPVLLPHQNGGLWMGPAGNHVPGLDLPPLD  351
Tomato-dCK/dGK   QVAEFFEFVKKKQEVMPGA--GEEQPKGNQAPVMLP-QGGLWVPGGKFSESTLNLDFRR   357
Pine-dCK/dGK     QVAEFFEVKRKEMQIE------DQTGNSKKLILP-QKGGL-LGPDGNFLRASQLNPLN    298
Maize-dCK/dGK    QVAEFFDFVKKKESLIKESETADGDKSINKQIVLP-HGGGLWVPGSS-PLPESALKSED   262
Rice-dCK/dGKII   QVAEFFEFVKKKKEDPSAE--SSGGDKSTNKQIMLP-HRGGLWVPSGN-PLPGSALNSLD  353
Rice-dCK/dGKI    QVAEFFQFVKKKEAPSEQ--ISTDKNRINPQIMLP-HRGGLWVPDGRNPFSGSAMN-LN    60
                 ***********************************************************
                 %%%:%%:%%%: :%  :           :   :: ::%%  : %%%  :  :      ::
```

TABLE 1-continued

Clustal W (1.8) Multiple Amino Acid Sequence Alignment

```
AT-dCK/dGK       LKSLLTRPSA-    361
Tomato-dCK/dGK   NMSFMSH----    364
Pine-dCK/dGK     FRQAISSR---    306
Maize-dCK/dGK    FRRTMSSST--    271
Rice-dCK/dGKII   FRRAMSSRLSA    364
Rice-dCK/dGKI    FRRAMSSRLST    71
                 ***********
                      : :
```

AT-dCK/dGK (SEQ ID NO: 2)
Tomato-dCK/dGK (SEQ ID NO: 6)
Pine-dCK/dGK (SEQ ID NO: 4)
Maize-dCK/dGK (SEQ ID NO: 8)
Rice-dCK/dGKII (SEQ ID NO: 12)
Rice-dCK/dGKI (SEQ ID NO: 10)
+N-terminal extension
*C-terminal extension
Black: identical residues - threshold 50%
Grey: similar residues - threshold 50%
% conserved residues
: semiconserved residues In a preferred embodiment the amino acid sequence of the plant deoxyribonucleoside kinase enzyme of the invention, when aligned with a sequence selected from those presented in Table 1, comprises 60% or more of the residues identified in Table 1 as conserved residues, preferably more than 70%, more preferred more than 80%, even more preferred more than 90%, still more preferred more than 95%, most preferred every one of the conserved residues identified in Table 1.

In a more preferred embodiment the amino acid sequence of the plant deoxyribonucleoside kinase enzyme of the invention, when aligned with a sequence selected from those presented in Table 1, in addition to comprising conserved residues, also comprises a semi-conserved residue at 60% or more of the positions identified in Table 1 as semi-conserved residues, preferably more than 70%, more preferred more than 80%, even more preferred more than 90%, still more preferred more than 95%, most preferred every one of the semi-conserved residues identified in Table 1.

Identity of Polypeptides

In another preferred embodiment the plant deoxyribonucleoside kinase enzyme of the invention comprises the amino acid sequence presented as SEQ ID NO: 2, as SEQ ID NO: 4, as SEQ ID NO: 6, as SEQ ID NO: 8, as SEQ ID NO: 10, or as SEQ ID NO: 12, or an amino acid sequence that has at least 80%, preferably at least 85%, more preferred at least 90%, most preferred at least 95% identity with any of said sequences, when determined over the entire length of the SEQ ID NO.

In the context of this invention "identity" is a measure of the degree of identical amino acid residues among sequences. In order to characterize the identity, subject sequences are aligned so that the highest order homology (match) is obtained. Based on these general principles the "percent identity" of two amino acid sequences is determined using the BLASTP algorithm [Tatiana A. Tatusova, Thomas L. Madden: Blast 2 sequences—a new tool for comparing protein and nucleotide sequences; FEMS Microbiol. Lett. 1999 174 247-250], which is available from the National Center for Biotechnology Information (NCBI) web site, and using the default settings suggested here (i.e. Matrix=Blosum62; Open gap=11; Extension gap=1; Penalties gab x_dropoff=50; Expect=10; Word size=3; Filter on). The BLAST algorithm determines the % sequence identity in a range of overlap between two aligned sequences. For the purposes of the present invention, the percent sequence identity is preferably calculated in a range of overlap of at least 50 amino acids, more preferably at least 75 amino acids, more preferably at least 100 amino acids, the range being calculated by BLASTP under default settings.

The results of these BLASTP determinations are presented in Tables 2A-2D below.

TABLE 2

BLASTP Comparison of Protein Sequences
Comparison of the full sequences presented in Table 1
Identities (%)/Positives (%)/length of the compared fragment

| DCK/dGK | Pine | Tomato | Maize | Rice I | Rice II |
|---------|------|--------|-------|--------|---------|
| AT | 75/85/288 | 79/89/346 | 75/86/256 | 50/66/55 | 77/88/349 |
| Pine | — | 75/85/307 | 69/82/269 | 48/67/68 | 72/82/309 |
| Tomato | — | — | 74/85/268 | 55/66/67 | 78/87/362 |
| Maize | — | — | — | 61/70/71 | 88/92/269 |
| Rice I | — | — | — | — | 54/65/71 |

In a preferred embodiment the plant deoxyribonucleoside kinase enzyme of the invention is derived from loblolly pine, and showing at least 76%, preferably at least 80%, more preferred at least 85%, even more preferred at least 90%, most preferred at least 95% identity with the amino acid residues presented in SEQ ID NO: 4, when determined over its entire length.

In another preferred embodiment the plant deoxyribonucleoside kinase enzyme of the invention is derived from tomato, and showing at least 80%, preferably at least 85%, more preferred at least 90%, most preferred at least 95% identity with the amino acid residues presented in SEQ ID NO: 6, when determined over its entire length.

In another preferred embodiment the plant deoxyribonucleoside kinase enzyme of the invention is derived from maize, and showing at least 76%, preferably at least 80%, more preferred at least 85%, even more preferred at least 90%, most preferred at least 95% identity with the amino acid residues presented in SEQ ID NO: 8, when determined over its entire length.

In another preferred embodiment the plant deoxyribonucleoside kinase enzyme of the invention is derived from rice, and showing at least 80%, preferably at least 85%, more preferred at least 90%, most preferred at least 95% identity with the amino acid residues presented in SEQ ID NO: 12, when determined over its entire length.

In another preferred embodiment the plant deoxyribonucleoside kinase enzyme of the invention is derived from rice, and showing at least 60%, more preferably at least 70% more preferably at least 80%, preferably at least 85%, more preferred at least 90%, most preferred at least 95% identity with the amino acid residues presented in SEQ ID NO: 10, when determined over its entire length.

In a preferred embodiment the plant deoxyribonucleoside kinase enzyme used for the pharmaceutical compositons and for medical and therapeutic use of the invention is derived from thale cress (*Arabidopsis thaliana*), and showing at least 76%, preferably at least 80%, more preferred at least 85%, even more preferred at least 90%, most preferred at least 95% identity with the amino acid residues presented in SEQ ID NO: 2, when determined over its entire length.

Variant Polypeptides

In a most preferred embodiment the plant deoxyribonucleoside kinase enzyme of the invention comprises the amino acid sequence presented as SEQ ID NO: 2, as SEQ ID NO: 4, as SEQ ID NO: 6, as SEQ ID NO: 8, as SEQ ID NO: 10, or as SEQ ID NO: 12, or a functional analogue thereof.

In the context of this invention, the term "functional analog" means a polypeptide (or protein) having an amino acid sequence that differs from the sequence presented as SEQ ID NO: 2, as SEQ ID NO: 4, as SEQ ID NO: 6, as SEQ ID NO: 8, as SEQ ID NO: 10, or as SEQ ID NO: 12, at one or more amino acid positions and has dCK/dGK activity. Such analogous polypeptides include polypeptides comprising conservative substitutions, splice variants, isoforms, homologues from other species, and polymorphisms.

As defined herein, the term "conservative substitutions" denotes the replacement of an amino acid residue by another, biologically similar residue. Examples of conservative substitutions include (i) the substitution of one non-polar or hydrophobic residue such as alanine, leucine, isoleucine, valine, proline, methionine, phenylalanine or tryptophan for another, in particular the substitution of alanine, leucine, isoleucine, valine or proline for another; or (ii) the substitution of one neutral (uncharged) polar residue such as serine, threonine, tyrosine, asparagine, glutamine, or cysteine for another, in particular the substitution of arginine for lysine, glutamic for aspartic acid, or glutamine for asparagine; or (iii) the substitution of a positively charged residue such as lysine, arginine or histidine for another; or (iv) the substitution of a negatively charged residue such as aspartic acid or glutamic acid for another.

The term conservative substitution also include the use of a substituted amino acid residue in place of a parent amino acid residue, provided that antibodies raised to the substituted polypeptide also immunoreact with the un-substituted polypeptide.

Modifications of this primary amino acid sequence may result in proteins which have substantially equivalent activity as compared to the unmodified counterpart polypeptide, and thus may be considered functional analogous of the parent proteins. Such modifications may be deliberate, e.g. as by site-directed mutagenesis, or they may occur spontaneous, and include splice variants, isoforms, homologues from other species, and polymorphisms. Such functional analogous are also contemplated according to the invention.

C- and N-terminal Deletions

According to the invention it has been found that plant deoxyribonucleoside kinase enzymes that are C- and/or N-terminally altered significantly change their properties in particular in respect of kinetic properties such as turnover and substrate specificity. So from having a more restricted specificity, usually deoxycytidine kinase (dCK) and deoxyguanosine kinase (dGK) activity, the plant deoxyribonucleoside kinase enzymes of the invention may be converted into essentially multi-substrate enzymes, having ability to phosphorylate all four deoxyribonucleosides.

In a preferred embodiment, the plant kinase enzyme of the invention, upon transduction into a cell, decreases at least 3 fold the lethal dose ($LD_{100}$) of at least one nucleoside analogue when compared to the action of a deoxyribonucleoside kinase derived from human Herpes simplex preferably human Herpes simplex virus type 1 (HSV-1).

In another embodiment the invention provides plant deoxyribonucleoside kinase enzymes having C- and/or N-terminal deletions when compared to the parent un-truncated (parent) enzyme. Such deletions may be obtained by conventional techniques, e.g. site-directed mutagenesis, or as described in the working examples.

In a preferred embodiment, the kinase enyme upon transduction into a cell dereceases at least 3 fold the lethal dose ($LD_{100}$) of at least one nucleoside analogue when compared to the action of the untruncated deoxyribonucleoside enzyme.

In a preferred embodiment, the kinase enzyme of the invention is plant deoxyribonucleoside kinase enzyme having a C-terminal and/or N-terminal deletion of up to about 100 amino acids. In a more preferred embodiment the kinase enzyme of the invention is plant deoxyribonucleoside kinase enzyme having a C-terminal deletion in the order of 1-80, preferably 1-60 amino acid residues, more preferred 1-50 amino acid residues, even more preferred 1-40 amino acid residues, still more preferred 1-30 amino acid residues, most preferred 1-20 amino acid residues. In a particularly preferred embodiment the kinase enzyme of the invention is plant deoxyribonucleoside kinase enzyme having a C-terminal deletion of 61 amino acid residues. In a particularly preferred embodiment said C-terminally deleted variant is derived from tomato.

In another preferred embodiment the kinase enzyme of the invention is plant deoxyribonucleoside kinase enzyme having a N-terminal deletion in the order of 1-80, preferably 1-60 amino acid residues, more preferred 1-50 amino acid residues, even more preferred 1-40 amino acid residues, still more preferred 1-30 amino acid residues, most preferred 1-20 amino acid residues. More preferably the N-terminally deleted variant dCK/dGK enzyme is derived from tomato.

According to the invention it has been found that C-terminal deletions create enzymes of changed and often broader substrate specificities, when compared to the un-truncated (parent) enzyme.

Polynucleotides Encoding Plant Deoxyribonucleoside Kinases

In one aspect the invention relates to isolated polynucleotides encoding a plant dCK7dGK-like deoxyribonucleoside kinase, which upon transduction into a cell decreases at least 3 fold the lethal dose ($LD_{100}$) of at least one nucleoside analogue when compared to the action of a deoxyribonucleoside kinase derived from human Herpes simplex virus type 1 (HSV-1).

In one aspect the invention relates to isolated polynucleotides encoding plant deoxyribonucleoside kinase enzymes derived from loblolly pine (*Pinus taeda*), from tomato (*Lycopersicum esculentum*), from maize (*Zea mays*) or from rice (*Oryza sativa*), preferably encoding the plant deoxyribonucleoside kinase enzyme of the invention.

Hybridisation Protocol

In one embodiment, the isolated polynucleotide of the invention is capable of hybridising with the polynucleotide sequence presented as SEQ ID NO: 1, as SEQ ID NO: 3, as SEQ ID NO: 5, as SEQ ID NO: 7, as SEQ ID NO: 9, or as SEQ ID NO: 11, or its complementary strand.

Hybridization should be accomplished under at least low stringency conditions, but preferably at medium or high stringency conditions.

Suitable experimental conditions for determining hybridisation at low, medium, or high stringency conditions, respectively, between a nucleotide probe and a homologous DNA or RNA sequence, involves pre-soaking of the filter containing the DNA fragments or RNA to hybridise in 5×SSC [Sodium chloride/Sodium citrate; cf. Sambrook et al.; *Molecular Cloning: A Laboratory Manual*, 2$^{nd}$ Ed., Cold Spring Harbor Lab., Cold Spring Harbor, N.Y. 1989] for 10 minutes, and prehybridization of the filter in a solution of 5×SSC, 5× Denhardt's solution [cf. Sambrook et al.; Op cit.], 0.5% SDS and 100 µg/ml of denatured sonicated salmon sperm DNA [cf. Sambrook et al.; Op cit.], followed by hybridisation in the same solution containing a concentration of 10 ng/ml of a random-primed [Feinberg A P & Vogelstein B; *Anal. Biochem.* 1983 132 6-13], $^{32}$P-dCTP-labeled (specific activity>1×10$^9$ cpm/µg) probe for 12 hours at approximately 45° C.

The filter is then washed twice for 30 minutes in 2×SSC, 0.5% SDS at a temperature of at least 55° C. (low stringency conditions), more preferred of at least 60° C. (medium stringency conditions), still more preferred of at least 65° C. (medium/high stringency conditions), even more preferred of at least 70° C. (high stringency conditions), and yet more preferred of at least 75° C. (very high stringency conditions).

Molecules to which the oligonucleotide probe hybridises under these conditions may be labelled to detect hybridisation. The complementary nucleic acids or signal nucleic acids may be labelled by conventional methods known in the art to detect the presence of hybridised oligonucleotides. The most common method of detection is the use of autoradiography with e.g. $^3$H, $^{125}$I, $^{35}$S, $^{14}$C, or $^{32}$P-labelled probes, which may then be detected using an X-ray film. Other labels include ligands, which bind to labelled antibodies, fluorophores, chemoluminescent agents, enzymes, or antibodies, which can then serve as specific binding pair members for a labelled ligand.

Identity of DNA Sequences

In another preferred embodiment, the isolated polynucleotide of the invention has at least 81%, preferably at least 85%, more preferred at least 90%, most preferred at least 95% identity to the polynucleotide sequence presented as SEQ ID NO: 1, as SEQ ID NO: 3, as SEQ ID NO: 5, as SEQ ID NO: 7, as SEQ ID NO: 9, or as SEQ ID NO: 11, when determined over the entire length of the SEQ ID NO:. For the purposes of the present invention the percent sequence identity is calculated when BLASTN provides a range of overlap of at least 100 nucleotides, the range being determined under default settings. More preferably the range of overlap is at least 150 nucleotides, more preferably at least 225 nucleotides, more preferably at least 300 nucleotides.

In the context of this invention, "identity" is a measure of the degree of homology of nucleotide sequences. In order to characterize the identity, subject sequences are aligned so that the highest order homology (match) is obtained. Based on these general principles, the "percent identity" of two amino acid sequences or of two nucleic acids is determined using the BLASTN algorithm [Tatiana A. Tatusova, Thomas L. Madden: Blast 2 sequences—a new tool for comparing protein and nucleotide sequences; *FEMS Microbiol. Lett.* 1999 174 247-250], which is available from the National Center for Biotechnology Information (NCBI) web site, and using the default settings suggested here (i.e. Reward for a match=1; Penalty for a match=−2; Strand option=both strands; Open gap=5; Extension gap=2; Penalties bap x_dropoff50; Expect=10; Word size=11; Filter on). The BLASTN algorithm determines the % sequence identity in a range of overlap between two aligned nucleotide sequences. For the purposes of the present invention the percent sequence identity is preferably calculated in a range of overlap of at least 100 nucleotides, the range being determined by BLASTN under default settings. More preferably the range of overlap is at least 300 nucleotides.

The results of such a BLASTN comparison are presented in Table 3.

TABLE 3

BLASTN Comparison of DNA Sequences
Comparison of the full sequences presented in Table 1
Identities (%)/length of the compared fragment

| dCK/dGK | Pine | Tomato | Maize | Rice I | Rice II |
|---|---|---|---|---|---|
| AT | 80/422* | 78/83* | 78/401* | n.d. | 81/74* |
|  | 79/143 | 77/807 | 77/187 |  | 80/544 |
|  |  |  |  |  | 79/193 |
| Pine | — | 75/766 | 79/278* | n.d. | 79/422* |
|  |  |  | 74/156 |  | 74/152 |
| Tomato | — | — | 79/381* | n.d. | 86/59* |
|  |  |  | 75/149 |  | 80/530 |
|  |  |  |  |  | 79/154 |
| Maize | — | — | — | 89/58 | 86/809 |
| Rice I | — | — | — | — | 76/200 |

*fragments sorted beginning from the 5 prime of the sequences
n.d. = no significant similarity detected Therefore, in a preferred embodiment, the isolated polynucleotide for medical/pharmaceutical use is derived from thale cress (*Arabidopsis thaliana*) and shows at least 70%, preferably at least 80%, more preferably at least 85%, more preferred at least 90%, most preferred at least 95% identity to the polynucleotide sequence presented as SEQ ID NO: 1, when determined over its entire length.

Therefore, in a preferred embodiment, the isolated polynucleotide of the invention is derived from loblolly pine and shows at least 81%, preferably at least 85%, more preferred at least 90%, most preferred at least 95% identity to the polynucleotide sequence presented as SEQ ID NO: 3, when determined over its entire length.

In another preferred embodiment, the isolated polynucleotide, of the invention is derived from tomato and shows at least 79%, preferably at least 80%, more preferred at least 85%, even more preferred at least 90%, most preferred at least 95% identity to the polynucleotide sequence presented as SEQ ID NO: 5, when determined over its entire length.

In another preferred embodiment, the isolated polynucleotide of the invention is derived from maize and shows at least 79%, preferably at least 80%, more preferred at least 85%, even more preferred at least 90%, most preferred at least 95% identity to the polynucleotide sequence presented as SEQ ID NO: 7, when determined over its entire length.

In another preferred embodiment, the isolated polynucleotide of the invention is derived from rice and shows at least 82%, preferably at least 85%, more preferred at least 90%, most preferred at least 95% identity to the polynucleotide sequence presented as SEQ ID NO: 11, when determined over its entire length.

In another preferred embodiment, the isolated polynucleotide of the invention is derived from rice and shows at least 82%, preferably at least 85%, more preferred at least 90%, most preferred at least 95% identity to the polynucleotide sequence presented as SEQ ID NO: 9, when determined over its entire length.

Analogous DNA Sequences

In its most preferred embodiment, the isolated polynucleotide of the invention comprises the polynucleotide sequence presented as SEQ ID NO: 1, as SEQ ID NO: 3, as SEQ ID NO: 5, as SEQ ID NO: 7, as SEQ ID NO: 9, or as SEQ ID NO: 11, or a functional analog thereof.

In the context of this invention, the term "functional analog" covers conservatively modified polynucleotides, and polynucleotides encoding functionally equivalent polypeptides. By functionally equivalent polypeptides is meant a polypeptide having dCK/dGK enzyme activity as herein defined.

In the context of this invention, the term "conservatively modified polynucleotides" refers to those nucleic acids which encode identical or essentially identical amino acid sequences, or where the nucleic acid does not encode an amino acid sequence, to essentially identical sequences.

Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein, which encodes a polypeptide, also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid, which encodes a polypeptide, is implicit in each described sequence.

Expression Vectors

In one aspect the invention provides recombinant expression vectors comprising the isolated polynucleotide of the invention and a promoter operably linked to the polynucleotide.

The isolated polynucleotides are selected from the group consisting of
  an isolated polynucleotide having the sequence of any of SEQ ID No. 3, 5, 7, 9,or 11,
  an isolated polynucleotide encoding a dCK/dGK kinase enzyme of the invention,
  an isolated polynucleotide which when aligned to any of the sequences SEQ ID No. 3, 5, 7, 9, or 11 has at least 90% sequence identity to said sequence in the range of overlap, and
  the complementary sequence of any of the above.

The expression vector of the invention preferably is one suitable for carrying out expression in a eukaryotic organism.

In a more preferred embodiment the expression vector of the invention is a viral vector, in particular a Herpes simplex viral vector, an adenoviral vector, an adenovirus-associated viral vector, a lentivirus vector, a retroviral vector or a vacciniaviral vector.

Packaging Cell Lines

In one aspect the invention provides packaging cell lines capable of producing an infective virion, which cell line comprises a vector of the invention.

Packaging cells refers to cells, which contains those elements necessary for production of infectious recombinant vira, which are lacking in a recombinant virus vector. Methods for preparing packaging cells are known in the prior art.

Host Cells

In one aspect the invention provides a host cell comprising the polynucleotide sequence of the invention or the vector of the invention. In a preferred embodiment, the invention provides an isolated host cell transduced, transfected, or transformed with the expression vector of the invention.

In a preferred embodiment the host cell of the invention is a eukaryotic cell, in particular a mammalian cell, an oocyte, or a yeast cell.

In a more preferred embodiment the host cell of the invention is a human cell, a dog cell, a monkey cell, a rat cell or a mouse cell.

Suicide Systems

One very important use of the dCK/dGK enzyme encoding genes of the present invention is for suicide systems in cell and gene based therapy. In all types of cell and gene therapy on mammals there is a need to have systems, which enable the irreversible killing of transplanted cells or cells which have been transduced by the gene therapy.

There are basically two types of cell based therapies which both can benefit from having a built-in suicide system based on the deoxyribonucleoside kinases according to the present invention. In replacement cell therapy, naked cells are transplanted into a subject to replace cells that have lost the ability to fulfil their function in the body or to replace dead cells. Once these cells have been transplanted and are fully integrated into the body of the subject they cannot easily be removed by surgical means. By having a built-in suicide system in which a kinase of the present invention is expressed constitutively or inducibly, the cells can be killed by administering to the individual a therapeutically effective amount of a nucleoside analog, such as Gemcitabine. The nucleoside analogue can be administered if the transplanted cells start to proliferate in an uncontrolled manner. One may also wish to terminate the treatment simply because there is no need for the replacement cells anymore or because further treatment is by some other route.

The other type of cell-based therapy includes therapeutic cells which are transplanted into the body to secrete e.g. a growth factor in a certain location. Often such therapeutic cells are encapsulated and can relatively easily be removed from the body again but the incorporation of a suicide system is preferred because the cells can be killed selectively without the use of surgery.

In in vivo gene therapy the same considerations apply as with replacement cell therapy. The incorporation of a suicide gene can be achieved by constructing a viral vector comprising both the therapeutic gene and a dCK/dGK according to the present invention. Preferably the therapeutic gene and the dCK/dGK are inserted under the control of the same promoter, optionally by separating them with an IRES construct.

In the cases where transplanted cells have been conditionally immortalised before transplantation there is a theoretical risk that the oncogene initiates transcription after transplantation and that the transplanted cells consequently become tumorigenic. Means to control this situation are made available by the present invention. Whenever cells are immortalised by transduction with an oncogene under the control of an inducible promoter (e.g. the Tet on-off system, the Mx1 promoter or the like), a dCK/dGK enzyme is inserted into the vector construct under the control of the same promoter (or using an IRES construct). This ensures that whenever the oncogene is transcribed, the deoxyribonucleoside kinase is also transcribed and the transduced and tumorigenic cells can be selectively killed by administering a nucleoside analogue, such as Gemcitabine.

Method of Phosphorylating Nucleosides

The deoxyribonucleoside kinase enzyme of the invention may find different utility, including both therapeutic and biotechnological applications.

In a final aspect the invention relates to use of the plant deoxyribonucleoside kinase enzyme of the invention for phosphorylating nucleosides or a nucleoside analogs.

In a preferred embodiment the invention provides a method for phosphorylating a nucleoside or a nucleoside analog, comprising the steps of
  i) subjecting the nucleoside or nucleoside analog to the action of the plant deoxyribonucleoside kinase enzyme of the invention; and
  ii) recovering the phosphorylated nucleoside or nucleoside analog.

Imaging

Suicide gene therapy, i.e. transfection of a so-called suicide gene that sensitizes target cells towards a prodrug, offers an attractive approach for treating malignant tumors. For the development of effective clinical suicide gene therapy protocols, a non-invasive method to assay the extent, the kinetics and the spatial distribution of transgene expression is essential. Such imaging methods allow investigators and physicians to assess the efficiency of experimental and therapeutic gene transfection protocols and would enable early prognosis of therapy outcome.

Radionuclide imaging techniques like single photon emission computed tomography (SPECT) and positron emission tomography (PET), which can non-invasively visualize and quantify metabolic processes in vivo, are being evaluated for repetitive monitoring of transgene expression in living animals and humans. Transgene expression can be monitored directly by imaging the expression of the therapeutic gene itself, or indirectly using a reporter gene that is coupled to the therapeutic gene. Various radiopharmaceuticals have been developed and are now being evaluated for imaging of transgene expression.

Therefore, in another aspect, the invention provides a method of non-invasive nuclear imaging of transgene expression of a plant deoxyribonucleoside kinase enzyme of the invention in a cell or subject, which method comprises the steps of
  (i) transfecting said cell or subject with a polynucleotide sequence encoding a plant deoxyribonucleoside kinase enzyme, which enzyme promotes the conversion of a substrate into a substrate-monophosphate,
  (ii) delivering said substrate to said cell or subject; and
  (iii) non-invasively monitoring the change to said prodrug in said cell or subject.

In a preferred embodiment the monitoring carried out in step (iii) is performed by Single Photon Emission Computed Tomography (SPECT), by Positron Emission Tomography (PET), by Magnetic Resonance Spectroscopy (MRS), by Magnetic Resonance Imaging (MRI), or by Computed Axial X-ray Tomography (CAT), or a combination thereof In a more preferred embodiment the substrate is a labelled nucleoside analogue selected from those listed above. The labelled nucleoside analogue preferably contains at least one radionuclide as a label. Positron emitting radionuclides are all candidates for usage. In the context of this invention the radionuclide is preferably selected from $^2H$ (deuterium), $^3H$ (tritium), $^{11}C$, $^{13}C$, $^{14}C$, $^{15}O$, $^{13}N$, $^{123}I$, $^{125}I$, $^{131}I$, $^{18}F$ and $^{99m}Tc$.

An example of commercially available labelling agents, which can be used in the preparation of the labelled nucleoside analogue is $[^{11}C]O_2$, $^{18}F$, and NaI with different isotopes of Iodine. In particular $[^{11}C]O_2$ may be converted to a $[^{11}C]$-methylating agent, such as $[^{11}C]H_3I$ or $[^{11}C]$-methyl triflate.

Genetically Modified Plants

The deoxyribonucleosides of the invention may also find utility in methods for modifying or controlling plant growth. Therefore, in a further aspect, the invention relates to a method of controlling or modifying growth of a plant, which plant comprises plant cells comprising a polynucleotide encoding a plant dCK/dGK enzyme of the invention, which method comprises the step of exposing the plant or plant cell to a nucleoside analog. By the discovery of hitherto unknown properties of plant deoxyribonucleoside kinases and in particular those described in the present invention, the inventors contemplate the use of nucleoside analogues as herbicides. As plant deoxyribonucleoside kinases convert nucleoside analogues into toxic substances, nucleoside analogues can be used as herbicides for plants having these dCK/dGK enzymes either by nature or as a heterologous gene. By inserting the deoxyribonucleoside kinases of the present invention into plants not having a deoxyribonucleoside kinase with these properties, the plant is rendered susceptible to nucleoside analogs.

The polynucleotide encoding plant dCK/dGK enzyme of the invention preferably is a heterologous polynucleotide, and the plant subjected to the method of the invention preferably is a transgenic plant.

Therefore, in a yet further aspect, the invention provides transgenic plants comprising an expressible heterologous nucleic acid encoding the plant deoxyribonucleoside enzyme of the invention, wherein the heterologous nucleic acid is introduced into the transgenic plant, or an ancestor of the transgenic plant.

The transgenic plant may be obtained by known techniques for producing genetically modified plants, e.g. by introducing into a plant cell an expression vector of the invention.

Any plant deoxyribonucleoside kinase may also be knocked out and/or functionally replaced by another plant dCK/dGK, said other kinase not being able to convert a certain nucleoside analog. A nucleoside analogue may then be used to kill all other plants around this genetically modified plant.

Any transformed plant obtained according to the invention can be used in a conventional breeding scheme or in vitro plant propagation to produce more transformed plants with the same characteristics and/or can be used to introduce the same characteristics in other varieties of the same or related species. Such plants are also part of the invention. Seeds obtained from the transformed plants contain the same genetical characteristics and also form part of the invention.

Preferably the polynucleotide sequence encoding a plant dCK/dGK is selected from the group consisting of:

a polynucleotide sequence represented by SEQ ID No 1 or 5;

a polynucleotide sequence having at least 80% sequence identity with SEQ ID No 1 or 5 when determined over its entire length;

a polynucleotide sequence derived from SEQ ID No 1 or 5 having a 5' and/or 3' deletion in the order of 3 to 240 nucleotides.

These polynucleotide sequences encode plant dCK/dGK enzymes with preferred kinetic properties.

More preferably, the polynucleotide sequence is derived from thale cress (*Arabidopsis thaliana*), which sequence shows at least 80%, preferably at least 85%, more preferred at least 90%, most preferred at least 95% identity with the polynucleotide sequence presented as SEQ ID No. 1. The thale cress dCK/dGK is the most efficient in terms of conversion of nucleoside analogs.

EXAMPLES

The invention is further illustrated with reference to the following examples, which are not intended to be in any way limiting to the scope of the invention as claimed.

Example 1

Identification and Determination of the Sequence of Plant dNK

When deposited sequences from *Arabidopsis thaliana* and *Lycopersicum esculentum* were analysed for homology to Dm-dNK (ACCN CAB41881), a putative deoxyribonucleoside kinase with a complete open reading frame (ORF) of 1086 bp (a protein of 361 amino acids with a calculated molecular mass of 41.2 kDa) was found for *Arabidopsis thaliana* (ACCN AAG51141), and an EST (ACCN AW223792, clone cLEN13L23) with 541 bp was found for *Lycopersicum esculentum*. The plasmid containing ACCN AW223792 (clone cLEN13L23) was obtained from the Clemson University Genomics Institute and the insert sequenced. For cLEN13L23 an ORF of 1098 bp encoding a protein of 365 amino acids with a calculated molecular mass of 42.2 kDa was found. The ORF was submitted to Gen-Bank™ with the ACCN AF514776 (SEQ ID NO 5).

When deposited plant EST sequences were analysed for homology with ACCN AF514776 from *Lycopersicum esculentum*, an EST (ACCN AW011158, clone ST17D06) with 594 bp from loblolly pine, an EST (ACCN AW036847) with 631 bp from maize, and an EST (ACCN C73813, clone E20207) with 455 bp from rice were found. The plasmid containing ACCN AW011158 was obtained from Ross Whetten, Forest Biotechnology Group, North Carolina State University, Dept. of Forestry, NC State University, 6113 Jordan Hall, Raleigh, N.C., 27695-8008. The plasmid containing ACCN AW036847 was obtained from V. Walbot, Department of Biological Sciences, Stanford University, 855 California Ave, Palo Alto, Calif. 94304, USA. The plasmid containing ACCN C73813 was obtained from Takuji Sasaki, National Institute of Agrobiological Resources, Rice Genome Research Program, Kannondai 2-1-2, Tsukuba, Ibaraki, 305-8602, Japan.

The inserts of the three plasmids were completely sequenced, and partial sequences for deoxyribonucleoside kinases (Loblolly pine, Maize and Rice I) were found (see SEQ ID NOS: 3, 7 and 9).

An alignment of the plant deoxyribonucleoside kinase sequences is presented in Table 1.

By comparing the full-length ORF of the *Arabidopsis thaliana* and *Lycopersicum esculentum* deoxyribonculeoside kinases to genomic sequences of rice, and by combining several DNA fragments from ACCN AP003922, the following full-length ORF for a deoxyribonucleoside kinase from rice presented as SEQ ID NO: 11 could be assembled, encoding the protein presented as SEQ ID NO: 12.

The fact that SEQ ID NO: 10 is not completely identical to SEQ ID NO 12 implies the existence of isoforms of rice deoxyribonculeoside kinases (Rice dNK I and Rice dNK II).

Example 2

Construction of Bacterial Expression Plasmids

This example describes the preparation of bacterial expression plasmids for full-length and N- and/or C-terminal truncated deoxyribonucleoside kinases. The deoxyribonucleoside kinase from Lycopersicum esculentum and its truncated mutants were amplified and subcloned as follows:

The ORF of AF514776 (SEQ ID NO 5) was amplified by PCR using the primers

TOMfor1:
(SEQ ID NO: 13)
5' TAT CGC GGA TCC ATG GTT GAG TTC TTG CAA AGC TCA ATT GGA 3',
and TOMrev1A:
(SEQ ID NO: 14)
5' CCG GAA TTC GTC GAC TTA GTG AGA CAT GAA TGA CAT ATT TC 3', and using clone cLEN13L23 as the template.

The PCR fragment was subsequently cut by EcoRI/BamHI and ligated into pGEX-2T vector (Amersham-Pharmacia) that was also cut by EcoRI/BamHI. The resulting plasmid was named pGEX-2T-TOM-dCK/dGK.

In analogy N and/or C-terminal deletions were done and the PCR fragments ligated into pGEX-2T.

For N-terminal deletion the primers

TOMDELfor:
(SEQ ID NO: 15)
5' TAT CGC GGA TCC GTG AAG TCA ACA CAA AAG AAA CGA CTT ACT 3',
and TOMrev1A (SEQ ID NO: 14) were used, the resulting plasmid was named pGEX-2T-TOM-ΔNdCK/dGK.

For C-terminal deletion the primers

TOMfor1 (SEQ ID NO: 13), and

TOMDELrev:
(SEQ ID NO: 16)
5' CCG GAA TCC TTA AGC AAC TTG ACG AGC ATA CTG CCT CTT TGC 3', were used, the resulting plasmid was named pGEX-2T-TOM-dCK/dGKΔC.

For N- and C-terminal deletion the primers TOMDELfor (SEQ ID NO: 15) and TOMDELrev (SEQ ID NO: 16) were used together, and the resulting plasmid was named pGEX-2T-TOM-ΔNdCK/dGKΔC.

The deoxyribonucleoside kinase from *Arabidopsis thaliana* was subcloned as follows. The ORF was amplified from a cDNA library (Stragene) using the following primers:

```
1MSAtdGK-B:
                                         (SEQ ID NO: 17)
5' CGC GGA TCC ATG GTT GAT TAT CTT AGG AGC TCT GTT
GGG 3'
and 2MSAtdGK-E:
                                         (SEQ ID NO: 18)
5' CCG GAA TTC TCA CGC AGA CGG TCT AGT GAG GAG TGA
CTT G 3'
```

The PCR fragment was subsequently cut by EcoRI/BamHI and ligated into pGEX-2T vector that was also cut by EcoRI/BamHI. The resulting plasmid was named pGEX-2T-AT-dCK/dGK.

For comparison an expression plasmid for human Herpes simplex virus type 1 thymidine kinase (HSV1-TK) was also constructed. The thymidine kinase from human HSV1 was amplified using the primers

```
HSV-for A:
                                         (SEQ ID NO: 19)
5' CGC GGA TCC ATG GCT TCG TAC CCC GGC CAT C 3',
and HSV-rev:
                                         (SEQ ID NO: 20)
5' CCG GAA TTC TTA GTT AGC CTC CCC CAT CTC CCG 3',
``` using the plasmid pCMV-pacTK described by Karreman [Christiaan Karreman; *Gene* 1998 218 57-62] as template.

The PCR fragment was subsequently cut by EcoRI/BamHI and ligated into pGEX-2T vector that was also cut by EcoRI/BamHI. The resulting plasmid was named pGEX-2T-HSV-TK.

Example 3

Recombinant Expression and Enzyme Assay

In this example the plant deoxyribonucleoside kinase enzymes of the invention are expressed and their activity characterised.

To investigate the importance of the N- and C-terminal parts of the plant dCK/dGK TOM-dCK/dGK was reduced stepwise to a core of 263 amino acids, which corresponds roughly the total length of other eukaryotic TK2 or dCK/dGK-like deoxyribonucleoside kinases.

The *E. coli* strain KY895 (F$^-$, tdk-1, ilv) [Knecht W, Munch-Petersen B and Piškur J: Identification of residues involved in the specificity and regulation of the highly efficient multisubstrate deoxyribonucleoside kinase from *Drosophila melanogaster*; *J. Mol. Biol.* 2000 301 827-837] was transformed by various expression plasmids using standard techniques. Transformed KY895 strains were grown to an OD600 nm of 0.5-0.6 in LB/Ampicillin (100 μg/ml) medium at 37° C., and protein expression was induced by addition of 100 μM IPTG. The cells were further grown for 4 hours at 25° C. and subsequently harvested by centrifugation.

Pellets were stored at −80° C. until activity testing. Pellets were submitted to brief sonification in extraction buffer (50 mM Tris/HCl pH 7.5, 1 mM DTT, 10% (v/v) glycerol, 1% (v/v) Triton X-100, protease inhibitor cocktail (Complete™ from Roche Diagnostics).

Deoxyribonucleoside kinase activities were determined in the KY895 extracts by initial velocity measurements based on four time samples by the DE-81 filter paper assay using tritium-labelled nucleoside substrates. 4 to 20 μg extracts were used in the assays. The assay was done as described by Munch-Petersen et al. [Munch-Petersen, B., Knecht, W, Lenz, C., Sondergaard, L. & Piskur, J: Functional expression of a multisubstrate deoxyribonucleoside kinase from *Drosophila melanogaster* and its C-terminal deletion mutants; *J. Biol. Chem.* 2000 275 6673-6679].

The protein concentration was determined according to Bradford with BSA as standard protein [Bradford M M: A rapid and sensitive method for the quantitation of microgram quantities of protein utilizing the principle of protein-dye binding; *Anal. Biochem.* 1976 72 248-254]. SDS-PAGE was done according to the procedure of Laemmli [Laemmli U K: Cleavage of structural proteins during the assembly of the head of bacteriophage T4; *Nature* 1970 227 680-685], and proteins were visualized by Coomassie staining to verify recombinant protein expression.

The four natural deoxyribonucleosides were tested at a fixed concentration of 100 μM. The highest specific activity in each extract was set to 100%.

The results of these experiments are presented in Table 4 below.

TABLE 4

| Deoxyribonucleoside Kinase Activity in Extracts of Transformed KY895 | | | | |
|---|---|---|---|---|
| Transformant* | dThd | dAdo | dGuo | dCyd |
| pGEX-2T | n.d. | n.d. | n.d. | n.d. |
| pGEX-2T-TOM-dCK/dGK | n.d. | 94 | 100 (3.3) | 68 |
| pGEX-2T-TOM-ΔNdCK/dGK | n.d. | 82 | 100 (0.32) | 69 |
| pGEX-2T-TOM-dCK/dGKΔC | 100 (0.27) | 64 | 74 | 50 |
| pGEX-2T-TOM-ΔNdCK/dGKΔC | n.d. | n.d. | n.d. | n.d. |
| pGEX-2T-AT-dCK/dGK | n.d. | 100 (1.9) | 91 | 77 |

*pGEX-2T is the vector and is available from Amersham-Pharmacia; pGEX-2T-TOM-dCK/dGK is the vector containing the gene encoding a tomato dNK enzyme;pGEX-2T-TOM-ΔNdCK/dGK is the vector containing a gene that has been N-terminally deleted, encoding a tomato dNK enzyme; pGEX-2T-TOM-dCK/dGKΔC is the vector containinga gene that has been C-terminally deleted, encoding a tomato dNK enzyme; pGEX-2T-TOM-ΔNdCK/dGKΔC is the vector containing a gene that has been an N-terminally deleted andC-terminally deleted, encoding a tomato dNK enzyme; and pGEX-2T-AT-dCK/dGK is the vector containing the gene encoding an *Arabidopsis thaliana* dNK enzyme.
The figures in parenthesis show the specific activity in mU/mg corresponding to 100%.
n.d. = not detectable.

The deoxyribonucleoside kinases from *Arabidopsis thaliana* (pGEX-2T-AT-dCK/dGK) and tomato (pGEX-2T-TOM-dCK/dGK and pGEX-2T-TOM-ΔNdCK/dGK) were able to phosphorylate dCyd, dAdo and dGuo, but not dThd. Deletion of the C-terminal part of the tomato dCK/dGK-like kinase (pGEX-2T-TOM-dCK/dGKΔC) resulted in significantly different substrate specificities, and dThd became the fastest converted substrate. This shows that the C-terminus is important in the determination of the substrate specificity.

In short, the extended N- and C-terminus together play a vital role in substrate specificity and structural integrity of plant deoxyribonucleoside kinases.

Example 4

Determination of $LD_{100}$ of Transformed KY895

Deoxyribonucleoside kinases are of interest as suicide-genes to be used in gene-mediated therapy of cancer or viral infections. In this example the potential of the plant kinases of the invention to convert different nucleoside analogs are compared to that of the human Herpes simplex virus type 1 thymidine kinase (HSV1-TK) in a bacterial test system.

The experiment was carried out essentially as described by Knecht et al. [Knecht W, Munch-Petersen B and Piškur J: Identification of residues involved in the specificity and regulation of the highly efficient multisubstrate deoxyribonucleoside kinase from Drosophila melanogaster; *J. Mol. Biol.* 2000 301 827-837]. Briefly, overnight cultures of transformed KY895 were diluted 200-filed in 10% glyercol and 2 µl drops of the dilutions were spotted on M9 minimal medium plates [Ausubel F, Brent R, Kingston R E, Moore D D, Seidman J G, Smith J A & Struhl K (Eds.): Short protocols in molecular biology; $3^{rd}$ edition (1995) pp. 1-2, Wiley, USA] supplemented with 0.2% glucose, 40 µg/ml isoleucine, 40 µg/ml valine, 100 µg/ml ampicillin and with or without nucleoside analogs. Growth was inspected visually after 24 hours of incubation at 37° C.

The results of the experiment are presented in Table 5 below.

TABLE 5

$LD_{100}$ Values for Growth of Transformed KY895 Cells on Nucleoside Analog dFdC

| Transformant* | dFdC (µM) |
|---|---|
| pGEX-2T | 100 |
| pGEX-2T-TOM-dCK/dGK | 10 |
| pGEX-2T-TOM-ΔNdCK/dGK | 10 |
| pGEX-2T-TOM-dCK/dGKΔC | 100 |
| pGEX-2T-TOM-ΔNdCK/dGKΔC | 100 |
| pGEX-2T-AT-dCK/dGK | 0.01 |
| pGEX-2T-HSV-TK | 100 |

*See comments to Table 4.

As can be seen from Table 5, AT-dCK/dGK was most efficient, as reflected by the lowest $LD_{100}$, in killing KY895 on dFdC plates. The $LD_{100}$ was 10000-fold lower than that of HSV1-TK, that sensitised the cells to the same degree as the empty plasmid pGEX-2T. Cells transfected with the expression plasmid for TOM-dCK/dGK or TOM-ΔNdCK/dGK could be killed at 10-fold lower concentrations than cells transformed with pGEX-2T-HSV-TK or pGEX-2T.

Example 5

Construction of a Retrovirus Vector Expressing Plant Kinases

The cDNA of plant kinases were cloned into a retrovirus vector based on the Moloney murine leukemia (MLV) virus to generate a replication-deficient recombinant retrovirus containing the kinases.

DNA fragments were amplified with Pfu polymerase (Stratagene) using primers with designed flanking restriction enzyme sites and containing Kozak sequence at 5' end.

*A. thaliana* and tomato constructs based on PCR fragment were cut with BamHI/XhoI and cloned into the BglII-XhoI site of the pLCXSN plasmid vector (NsGene A/S) under the control of CMV promoter.

Two constructs were obtained: AtdCGK (PZG190) and TomdCGK (PZG193). LCXSN alone was used as a control.

The plasmids were purified using the Qiagen plasmid kit (QIAGEN) and DNA sequences of the constructed plasmids were verified by DNA sequence determination.

The following primer sequences were used:

```
At dCK/dGK + Kozak
5' TCCCTCGAGCGCCATGGTTGATTATCTTAGGAGC 3'
(SEQ ID NO:21)

At dCK/dGK 3'end
5' CGGGATCCTCACGCAGACGGTCTAGTGAGGAG 3'
(SEQ ID NO:22)

Tomato dCK/dGK + Kozak
5' TCCCTCGAGCGCCATGGTTGAGTTCTTGCAAAGC 3'
(SEQ ID NO:23)

Tomato dCK/dGK 3'end
5' CGGGATCCTTAGTGAGACATGAATGACATATTTC 3'
(SEQ ID NO:24)
```

HE 293 T packaging cells (ATCC CRL-11268) were cultured at 37° C. inOPTIMEM 1 medium (Life Technologies, Inc.) The constructed pLCXSN plasmid vector was transfected into the packaging cells using LipofectAMINE PLUS (Life Technologies, Inc.) according to the protocol provided by the supplier. The medium from the transfected cells was collected 48 hours after transfection, filtered through a 0.45 µm filter, pelleted by ultracentrifugation (50.000×g, 90 minutes at 4° C.) and dissolved in DMEM (Cambrex, Bio Whittaker Cat. No. 12-741-F).

The virus containing medium was subsequently used to transduce the cancer cell lines with a MOI of 5.

Cell Culture and Retroviral Transduction

Human breast MCF-7 (ATCC HTB-22) and Glioblastoma U-118-MG (ATCC HTB-15) cancer cells were purchased from the American Type Culture Collection. Cells were cultured in RPMI, E-MEM or D-MEM (Cambrex, Bio Whittaker Cat. No. 12-115-F, 12-611 and 12-741-F) with 10% (v/v) Australian originated fetal calf serum (Cambrex, Bio Whittaker Cat. No. 12-611) and 1 ml/l of Gentamicin (Cambrex, Bio Whittaker Cat. No. 17-518). Cells were grown at 37° C. in a humidified incubator with a gas phase of 5% $CO_2$.

The cells were transduced with the retrovirus containing medium mixed with 5 µg/ml of Polybrene, incubated for 48 hours and then cultured continuously for 3 weeks in the presence of 300-400 µg/ml Genetecin® (Life Technologies Inc.).

Cell Proliferation Assay—Cytotoxicity

Cells were plated at densities range of 1.500-3.500 cells/well in 96-well plates coated with Poly-L-lysine (Sigma Cat. No. P6282) Gemcitabine (obtained from Orifarm A/S—DK) was added after 24 hours of incubation at 37° C., 5% $CO_2$, and the medium containing the nucleoside analog. Each experiment was performed in four replicates. Cell survival was assayed after 96-120 hours of drug exposure, by XTT cell proliferation kit (X) kit II, Roche Cat. No. 1 465 015). The data was corrected for background media-only absorbance where after the 50% cell killing drug concentration—($IC_{50}$ value) was calculated. The $IC_{50}$ value of the investigated drug/compound was calculated as the mean of these experiments using SigmaPlot®) (SPSS Science, Dyrberg Traiding—DK).

Expression of Plant dCGK

The sensitivity of the untransduced cells, and of the cells transduced with either the retroviral vector alone ore the vector containing plant kinases for Gemcitabine was determined.

The cytotoxicity ($IC_{50}$ value) was determined after 96-120 hours of drug exposure. The results are presented in the table below.

TABLE 6

Sensitivity ($IC_{50}$) of the Glioma and Breast cell lines to Gemcitabine The concentrations which cause 50% lethality are shown for each construct and the parental cell line. The factor of sensitivity increase is compared to the parental cell line.

| | $IC_{50}$ value | Sensitivity factor |
|---|---|---|
| U-118-MG | | |
| Parental | 0.0062 µM | — |
| PZG190 | 0.0003 µM | 20-fold |

TABLE 6-continued

Sensitivity ($IC_{50}$) of the Glioma and Breast cell lines to Gemcitabine The concentrations which cause 50% lethality are shown for each construct and the parental cell line. The factor of sensitivity increase is compared to the parental cell line.

| | $IC_{50}$ value | Sensitivity factor |
|---|---|---|
| MCF-7 | | |
| Parental | 3.1157 mM | — |
| PZG190 | 0.5000 mM | 6-fold |
| PZG193 | 0.4025 mM | 8-fold |

The difference in sensitivity between the parental cell line and the cells transduced with the pLCXSN vector alone was less than 1-fold.

The cell lines expressing the plant kinases, showed an increase in sensitivity to Gemcitabine. The highest increase was detected in the glioma cell line (U-118-MG) expressing *Arabidopsis thaliana* dCK (PZG190) with a 20-fold -increase in $IC_{50}$ compared with the untransduced cells.

The invention claimed is:

1. An isolated deoxyribonucleoside kinase enzyme comprising a contiguous amino acid sequence which, when aligned with SEQ ID NO:6 according to the BLASTP algorithm using the scoring matrix BLOSUM62, open gap penalty 11, extension gap penalty 1, the highest scoring alignment yields a percentage identity in the range of overlap which, as calculated by the NCBI implementation of BLASTP, is at least 80%, and such range of overlap is at least 50 amino acids, and which enzyme has dCK/dGK-like deoxyribonucleoside kinase activity wherein the percentage identity, determined over the entire length of SEQ ID NO:6, is at least 80%.

2. The enzyme according to claim 1, wherein the dCK/dGK-like deoxyribonucleoside kinase enzyme, upon transduction into a cell, decreases at least 10 fold the lethal dose (LD100) of at least one nucleoside analogue when compared to the action of a deoxyribonucleoside kinase derived from human Herpes simplex virus type 1 (HSV-1).

3. The enzyme of claim 2, wherein the nucleoside analogue is Gemcitabine (dFdC).

4. The enzyme according to claim 1, wherein the enzyme has a C-terminal deletion of 1-61 amino acid residues when compared to the parent, untruncated enzyme of SEQ ID NO:6.

5. The enzyme according to claim 1, wherein the deoxyribonucleoside kinase has an amino acid sequence which, when aligned with a sequence selected from those presented in Table 1, comprises 60% or more of the residues identified in Table 1 as conserved residues.

6. The enzyme according to claim 5, wherein the plant deoxyribonucleoside kinase has an amino acid sequence which also comprises a semi-conserved residue at 60% or more of the positions identified in Table 1 as semi-conserved residues.

7. The enzyme according to claim 1, wherein the enzyme has an N-terminal deletion of 1-60 amino acid residues when compared to the parent, untruncated enzyme of SEQ ID NO:6.

8. Articles comprising a nucleoside analogue and the deoxyribonucleoside kinase of claim 1.

9. Articles of claim 8, wherein the nucleoside analogue is selected from the group consisting of cytidine analogs, adenosine analogs and guanosine analogs.

10. The enzyme of claim 1, wherein the percentage identity in the range of overlap is at least 85%.

11. The enzyme of claim 1, wherein the percentage identity in the range of overlap is at least 90%.

12. The enzyme of claim 1, wherein the percentage identity in the range of overlap is at least 95%.

13. The enzyme of claim 1, wherein the percentage identity, determined over the entire sequence of SEQ ID NO:6, is at least 85%.

14. The enzyme of claim 1, wherein the percentage identity, determined over the entire sequence of SEQ ID NO:6, is at least 90%.

15. The enzyme of claim 1, wherein the percentage identity, determined over the entire sequence of SEQ ID NO:6, is at least 95%.

16. The enzyme of claim 1 which comprises SEQ ID NO:6.

17. The enzyme of claim 1, having an amino acid sequence such that when said sequence is aligned as stated with SEQ ID NO:6, it is identical with SEQ ID NO:6 at least 60% of the positions identified in Table 1 as conserved residues.

18. The enzyme of claim 1, having an amino acid sequence such that when said sequence is aligned as stated with SEQ ID NO:6, it is identical with SEQ ID NO:6 at least 70% of the positions identified in Table 1 as conserved residues.

19. The enzyme of claim 1, having an amino acid sequence such that when said sequence is aligned as stated with SEQ ID NO:6, it is identical with SEQ ID NO:6 at least 80% of the positions identified in Table 1 as conserved residues.

20. The enzyme of claim 1, having an amino acid sequence such that when said sequence is aligned as stated with SEQ ID NO:6, it is identical with SEQ ID NO:6 at least 90% of the positions identified in Table 1 as conserved residues.

21. The enzyme of claim 1, having an amino acid sequence such that when said sequence is aligned as stated with SEQ ID NO:6, it is identical with SEQ ID NO:6 at least 95% of the positions identified in Table 1 as conserved residues.

22. The enzyme of claim 1 wherein, when said sequence is aligned as stated with SEQ ID NO:6, at least 60% of the positions identified in Table 1 as semi conserved residues, it has one of the residues set forth in table 1 as occurring in the position of at least one of SEQ ID NOs:2, 4, 6, 8, 10, or 12 which is aligned in Table 1 with that position in SEQ ID NO:6.

23. The enzyme of claim 1 wherein, when said sequence is aligned as stated with SEQ ID NO:6, at least 70% of the positions identified in Table 1 as semi conserved residues, it has one of the residues set forth in Table 1 as occurring in position of at least one of SEQ ID NOs:2, 4, 6, 8, 10, or 12 which is aligned in Table 1 with that position in SEQ ID NO:6.

24. The enzyme of claim 1 wherein, when said sequence is aligned as stated with SEQ ID NO:6, at least 80% of the positions identified in Table 1 as semi conserved residues, it has one of the residues set forth in Table 1 as occurring in the position of at least one of SEQ ID NOs:2, 4, 6, 8, 10, or 12 which is aligned in Table 1 with that position in SEQ ID NO:6.

25. The enzyme of claim 1 wherein, when said sequence is aligned as stated with SEQ ID NO:6, at least 90% of the positions identified in Table 1 as semi conserved residues, it has one of the residues set forth in Table 1 as occurring in the position of at least one of SEQ ID NOs:2, 4, 6, 8, 10, or 12 which is aligned in Table 1 with that position in SEQ ID NO:6.

26. The enzyme of claim 1 wherein, when said sequence is aligned as stated with SEQ ID NO:6, at least 95% of the positions identified in Table 1 as semi conserved residues, it has one of the residues set forth in Table 1 as occurring in the position of at least one of SEQ ID NOs:2, 4, 6, 8, 10, or 12 which is aligned in Table 1 with that position in SEQ ID NO:6.

27. The enzyme of claim 1 wherein, when said sequence is aligned as stated with SEQ ID NO:6, at least 100% of the positions identified in Table 1 as semi conserved residues, it has one of the residues set forth in Table 1 as occurring in the position of at least one of SEQ ID NOs:2, 4, 6, 8, 10, or 12 which is aligned in Table 1 with that position in SEQ ID NO:6.

28. The enzyme of claim 1 which comprises a sequence which differs from SEQ ID NO:6 solely by one or more of the following substitutions:
  (i) of an amino acid selected from the group of nonpolar amino acids consisting of alanine, leucine, isoleucine, valine, proline, methionine, phenylalanine and tryptophan, for a different amino acid of the same group;
  (ii) of an amino acid selected from the group of uncharged polar amino acids consisting of serine, threonine, tyrosine, asparagine, glutamine and cysteine for a different amino acid of the same group;
  (iii) of an amino acid selected from the group of positively charged amino acids consisting of lysine, arginine and histidine for another of the same group;
  (iv) of aspartic acid for glutamic acid, or vice versa.

29. The enzyme of claim 1 which consists of SEQ ID NO:6.

30. The enzyme of claim 1 which comprises a continuous amino acid sequence which differs from amino acids 41-364 of SEQ ID NO:6 or amino acids 1-303 of SEQ ID NO:6, if at all, solely by one or more amino acid substitutions.

* * * * *

UNITED STATES PATENT AND TRADEMARK OFFICE
CERTIFICATE OF CORRECTION

PATENT NO. : 7,666,639 B2
APPLICATION NO. : 10/519395
DATED : February 23, 2010
INVENTOR(S) : Knecht et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 464 days.

Signed and Sealed this

Seventh Day of December, 2010

David J. Kappos
*Director of the United States Patent and Trademark Office*

SEQUENCE LISTING

```
<160> NUMBER OF SEQ ID NOS: 24

<210> SEQ ID NO 1
<211> LENGTH: 1086
<212> TYPE: DNA
<213> ORGANISM: Arabidopsis thaliana
<220> FEATURE:
<221> NAME/KEY: CDS
<222> LOCATION: (1)..(1086)

<400> SEQUENCE: 1 atg gtt gat tat ctt agg agc tct gtt ggg att ata cat aga aac cat      48
Met Val Asp Tyr Leu Arg Ser Ser Val Gly Ile Ile His Arg Asn His
1               5                   10                  15 gcg gag agt ata aca acg ttt att aaa gag agt gtg gat gat gag ctt      96
Ala Glu Ser Ile Thr Thr Phe Ile Lys Glu Ser Val Asp Asp Glu Leu
                20                  25                  30 aag gat tct ggc cct gaa cct aat cta aat gtg aag aaa cgt ttg acg     144
Lys Asp Ser Gly Pro Glu Pro Asn Leu Asn Val Lys Lys Arg Leu Thr
            35                  40                  45 ttt tgt gtt gaa ggg aac atc agt gtt ggt aaa tca act ttt ctt cag     192
Phe Cys Val Glu Gly Asn Ile Ser Val Gly Lys Ser Thr Phe Leu Gln
        50                  55                  60 agg ata gcg aat gag act gtt gag tta caa gac ctt gtt gag att gtt     240
Arg Ile Ala Asn Glu Thr Val Glu Leu Gln Asp Leu Val Glu Ile Val
65                  70                  75                  80 cct gag cca gtt gat aag tgg caa gat gtt gga cct gac cat ttc aat     288
Pro Glu Pro Val Asp Lys Trp Gln Asp Val Gly Pro Asp His Phe Asn
                85                  90                  95 ata ttg gat gct ttc tac tct gag cct cag agg tat gct tat act ttc     336
Ile Leu Asp Ala Phe Tyr Ser Glu Pro Gln Arg Tyr Ala Tyr Thr Phe
                100                 105                 110 cag aac tat gtg ttt gtc act cgg ctg atg cag gag aaa gag tct gct     384
Gln Asn Tyr Val Phe Val Thr Arg Leu Met Gln Glu Lys Glu Ser Ala
```

```
                 115                 120                 125
tct ggg gtt aaa cct ctc agg ttg atg gaa agg agt gtc ttc agt gac    432
Ser Gly Val Lys Pro Leu Arg Leu Met Glu Arg Ser Val Phe Ser Asp
    130                 135                 140 cga atg gtg ttt gtg cgt gcg gtt cat gaa gcg aaa tgg atg aat gag    480
Arg Met Val Phe Val Arg Ala Val His Glu Ala Lys Trp Met Asn Glu
145                 150                 155                 160 atg gag atc agc att tac gac tct tgg ttt gat ccg gtt gtc tct tct    528
Met Glu Ile Ser Ile Tyr Asp Ser Trp Phe Asp Pro Val Val Ser Ser
                165                 170                 175 tta cct gga ctt gtt cct gat ggg ttt ata tac tta agg gcg agt cca    576
Leu Pro Gly Leu Val Pro Asp Gly Phe Ile Tyr Leu Arg Ala Ser Pro
        180                 185                 190 gac act tgc cac aag cga atg atg ctc agg aaa cga gca gaa gaa ggc    624
Asp Thr Cys His Lys Arg Met Met Leu Arg Lys Arg Ala Glu Glu Gly
    195                 200                 205 gga gtc tct ctg aaa tac ctc caa gat ttg cac gag aag cac gag agc    672
Gly Val Ser Leu Lys Tyr Leu Gln Asp Leu His Glu Lys His Glu Ser
210                 215                 220 tgg ctg ctt ccc ttt gag agc gga aac cat ggt gta ttg tct gtt agt    720
Trp Leu Leu Pro Phe Glu Ser Gly Asn His Gly Val Leu Ser Val Ser
225                 230                 235                 240 aga cca tct tta cac atg gac aac tct ctg cat cct gat ata aag gac    768
Arg Pro Ser Leu His Met Asp Asn Ser Leu His Pro Asp Ile Lys Asp
                245                 250                 255 cgt gtc ttt tac ttg gaa gga aat cat atg cat tct agt atc cag aag    816
Arg Val Phe Tyr Leu Glu Gly Asn His Met His Ser Ser Ile Gln Lys
        260                 265                 270 gtc cct gct ctg gtt ttg gac tgt gaa ccc aat atc gac ttc agc cgg    864
Val Pro Ala Leu Val Leu Asp Cys Glu Pro Asn Ile Asp Phe Ser Arg
    275                 280                 285 gat att gaa gca aag aca cag tat gca cgc cag gtc gct gag ttc ttt    912
Asp Ile Glu Ala Lys Thr Gln Tyr Ala Arg Gln Val Ala Glu Phe Phe
290                 295                 300 gag ttt gtg aag aag aag caa gaa aca tct aca gag aag agc aac agt    960
Glu Phe Val Lys Lys Lys Gln Glu Thr Ser Thr Glu Lys Ser Asn Ser
305                 310                 315                 320 cag tcg ccg gta ctg cta cca cat cag aat gga ggt ctc tgg atg gga   1008
Gln Ser Pro Val Leu Leu Pro His Gln Asn Gly Gly Leu Trp Met Gly
                325                 330                 335 cca gca ggc aat cat gtc ccg gga tta gat ctc ccg cct cta gat ctc   1056
Pro Ala Gly Asn His Val Pro Gly Leu Asp Leu Pro Pro Leu Asp Leu
        340                 345                 350 aag tca ctc ctc act aga ccg tct gcg tga                           1086
Lys Ser Leu Leu Thr Arg Pro Ser Ala
    355                 360

<210> SEQ ID NO 2
<211> LENGTH: 361
<212> TYPE: PRT
<213> ORGANISM: Arabidopsis thaliana

<400> SEQUENCE: 2

Met Val Asp Tyr Leu Arg Ser Ser Val Gly Ile Ile His Arg Asn His
1               5                   10                  15

Ala Glu Ser Ile Thr Thr Phe Ile Lys Glu Ser Val Asp Asp Glu Leu
            20                  25                  30

Lys Asp Ser Gly Pro Glu Pro Asn Leu Asn Val Lys Lys Arg Leu Thr
        35                  40                  45
```

```
Phe Cys Val Glu Gly Asn Ile Ser Val Gly Lys Ser Thr Phe Leu Gln
 50                  55                  60

Arg Ile Ala Asn Glu Thr Val Glu Leu Gln Asp Leu Val Glu Ile Val
 65                  70                  75                  80

Pro Glu Pro Val Asp Lys Trp Gln Asp Val Gly Pro Asp His Phe Asn
                 85                  90                  95

Ile Leu Asp Ala Phe Tyr Ser Glu Pro Gln Arg Tyr Ala Tyr Thr Phe
            100                 105                 110

Gln Asn Tyr Val Phe Val Thr Arg Leu Met Gln Glu Lys Glu Ser Ala
        115                 120                 125

Ser Gly Val Lys Pro Leu Arg Leu Met Glu Arg Ser Val Phe Ser Asp
    130                 135                 140

Arg Met Val Phe Val Arg Ala Val His Glu Ala Lys Trp Met Asn Glu
145                 150                 155                 160

Met Glu Ile Ser Ile Tyr Asp Ser Trp Phe Asp Pro Val Val Ser Ser
                165                 170                 175

Leu Pro Gly Leu Val Pro Asp Gly Phe Ile Tyr Leu Arg Ala Ser Pro
            180                 185                 190

Asp Thr Cys His Lys Arg Met Met Leu Arg Lys Arg Ala Glu Glu Gly
        195                 200                 205

Gly Val Ser Leu Lys Tyr Leu Gln Asp Leu His Glu Lys His Glu Ser
    210                 215                 220

Trp Leu Leu Pro Phe Glu Ser Gly Asn His Gly Val Leu Ser Val Ser
225                 230                 235                 240

Arg Pro Ser Leu His Met Asp Asn Ser Leu His Pro Asp Ile Lys Asp
                245                 250                 255

Arg Val Phe Tyr Leu Glu Gly Asn His Met His Ser Ser Ile Gln Lys
            260                 265                 270

Val Pro Ala Leu Val Leu Asp Cys Glu Pro Asn Ile Asp Phe Ser Arg
        275                 280                 285

Asp Ile Glu Ala Lys Thr Gln Tyr Ala Arg Gln Val Ala Glu Phe Phe
    290                 295                 300

Glu Phe Val Lys Lys Lys Gln Glu Thr Ser Thr Glu Lys Ser Asn Ser
305                 310                 315                 320

Gln Ser Pro Val Leu Leu Pro His Gln Asn Gly Gly Leu Trp Met Gly
                325                 330                 335

Pro Ala Gly Asn His Val Pro Gly Leu Asp Leu Pro Pro Leu Asp Leu
            340                 345                 350

Lys Ser Leu Leu Thr Arg Pro Ser Ala
        355                 360

<210> SEQ ID NO 3
<211> LENGTH: 921
<212> TYPE: DNA
<213> ORGANISM: Pinus taeda
<220> FEATURE:
<221> NAME/KEY: CDS
<222> LOCATION: (1)..(921)

<400> SEQUENCE: 3 aat att agt gtt ggg aaa acc aca ttt cta cag agg att gcg aat gag      48
Asn Ile Ser Val Gly Lys Thr Thr Phe Leu Gln Arg Ile Ala Asn Glu
 1               5                  10                  15 aca ctt gag tta cgt gac ctc gta gag gtg gtt cct ggg cct att tct      96
Thr Leu Glu Leu Arg Asp Leu Val Glu Val Val Pro Gly Pro Ile Ser
            20                  25                  30
```

```
aag tgg caa gac att ggg cct gat cat ttc aat ata ttg gat gct ttc      144
Lys Trp Gln Asp Ile Gly Pro Asp His Phe Asn Ile Leu Asp Ala Phe
         35                  40                  45 tat gct gaa cct caa cgg tat gcc tac aca ttc cag aat tat gtt ttt      192
Tyr Ala Glu Pro Gln Arg Tyr Ala Tyr Thr Phe Gln Asn Tyr Val Phe
 50                  55                  60 gta acg agg gtg atg caa gag cga gag tct gca ggt agc tta aag cct      240
Val Thr Arg Val Met Gln Glu Arg Glu Ser Ala Gly Ser Leu Lys Pro
 65                  70                  75                  80 tta cga ctc atg gaa aga agt gtt ttc agt gat cgg atg gtg ttt gtg      288
Leu Arg Leu Met Glu Arg Ser Val Phe Ser Asp Arg Met Val Phe Val
                 85                  90                  95 cga gct gtt cat gag gca aag tgg atg aat ggg atg gag ctt agc atc      336
Arg Ala Val His Glu Ala Lys Trp Met Asn Gly Met Glu Leu Ser Ile
            100                 105                 110 tat gat tca tgg ttt gat cca gtt gtt tct gtt tta cct ggg ctt gtt      384
Tyr Asp Ser Trp Phe Asp Pro Val Val Ser Val Leu Pro Gly Leu Val
        115                 120                 125 ccc gat gga ttt att tac ttg agg gcc agt cca gac aca tgc cat aga      432
Pro Asp Gly Phe Ile Tyr Leu Arg Ala Ser Pro Asp Thr Cys His Arg
    130                 135                 140 gct ttg cag tta cga aag aga gaa gaa gaa aat agt gtg tca tta gat      480
Ala Leu Gln Leu Arg Lys Arg Glu Glu Glu Asn Ser Val Ser Leu Asp
145                 150                 155                 160 tat ttg aga ggt ttg cat gaa aag cat gag aac tgg ctc ttc cct gct      528
Tyr Leu Arg Gly Leu His Glu Lys His Glu Asn Trp Leu Phe Pro Ala
                165                 170                 175 gaa tgt ggt agt cat ggg ttg ttg tct gtg agc caa tta cct ctt gat      576
Glu Cys Gly Ser His Gly Leu Leu Ser Val Ser Gln Leu Pro Leu Asp
            180                 185                 190 att gat agg tct ctg cat cct gag atc aga gat cgc acg ttt ctt ttg      624
Ile Asp Arg Ser Leu His Pro Glu Ile Arg Asp Arg Thr Phe Leu Leu
        195                 200                 205 caa gga gat cat gta cat gct agt att cag aag gtt cca gca tta gtg      672
Gln Gly Asp His Val His Ala Ser Ile Gln Lys Val Pro Ala Leu Val
    210                 215                 220 ctg gat tgt gag ccc aat att gac ttc agc aga gac att gaa gca aag      720
Leu Asp Cys Glu Pro Asn Ile Asp Phe Ser Arg Asp Ile Glu Ala Lys
225                 230                 235                 240 caa gga tat gct cgt cag gtt gct gaa ttt ttt gaa ttt gtg aaa aga      768
Gln Gly Tyr Ala Arg Gln Val Ala Glu Phe Phe Glu Phe Val Lys Arg
                245                 250                 255 atg aaa gaa atg cag act cca gat caa gat act ggg aac tct aaa aag      816
Met Lys Glu Met Gln Thr Pro Asp Gln Asp Thr Gly Asn Ser Lys Lys
            260                 265                 270 ttg ata ctg cct caa aag ggt ggt tta cta ggt ccc gat ggc aac ttt      864
Leu Ile Leu Pro Gln Lys Gly Gly Leu Leu Gly Pro Asp Gly Asn Phe
        275                 280                 285 tta cga gcg tcg cag ctt aat cct tta aac ttt gcc cag gcc att tct      912
Leu Arg Ala Ser Gln Leu Asn Pro Leu Asn Phe Arg Gln Ala Ile Ser
    290                 295                 300 tct ttc tga                                                          921
Ser Phe
305

<210> SEQ ID NO 4
<211> LENGTH: 306
<212> TYPE: PRT
<213> ORGANISM: Pinus taeda

<400> SEQUENCE: 4
```

```
Asn Ile Ser Val Gly Lys Thr Thr Phe Leu Gln Arg Ile Ala Asn Glu
1               5                   10                  15

Thr Leu Glu Leu Arg Asp Leu Val Glu Val Pro Gly Pro Ile Ser
            20                  25                  30

Lys Trp Gln Asp Ile Gly Pro Asp His Phe Asn Ile Leu Asp Ala Phe
        35                  40                  45

Tyr Ala Glu Pro Gln Arg Tyr Ala Tyr Thr Phe Gln Asn Tyr Val Phe
    50                  55                  60

Val Thr Arg Val Met Gln Glu Arg Glu Ser Ala Gly Ser Leu Lys Pro
65                  70                  75                  80

Leu Arg Leu Met Glu Arg Ser Val Phe Ser Asp Arg Met Val Phe Val
                85                  90                  95

Arg Ala Val His Glu Ala Lys Trp Met Asn Gly Met Glu Leu Ser Ile
                100                 105                 110

Tyr Asp Ser Trp Phe Asp Pro Val Val Ser Val Leu Pro Gly Leu Val
            115                 120                 125

Pro Asp Gly Phe Ile Tyr Leu Arg Ala Ser Pro Asp Thr Cys His Arg
130                 135                 140

Ala Leu Gln Leu Arg Lys Arg Glu Glu Glu Asn Ser Val Ser Leu Asp
145                 150                 155                 160

Tyr Leu Arg Gly Leu His Glu Lys His Glu Asn Trp Leu Phe Pro Ala
                165                 170                 175

Glu Cys Gly Ser His Gly Leu Leu Ser Val Ser Gln Leu Pro Leu Asp
            180                 185                 190

Ile Asp Arg Ser Leu His Pro Glu Ile Arg Asp Arg Thr Phe Leu Leu
        195                 200                 205

Gln Gly Asp His Val His Ala Ser Ile Gln Lys Val Pro Ala Leu Val
    210                 215                 220

Leu Asp Cys Glu Pro Asn Ile Asp Phe Ser Arg Asp Ile Glu Ala Lys
225                 230                 235                 240

Gln Gly Tyr Ala Arg Gln Val Ala Glu Phe Phe Glu Phe Val Lys Arg
                245                 250                 255

Met Lys Glu Met Gln Thr Pro Asp Gln Asp Thr Gly Asn Ser Lys Lys
            260                 265                 270

Leu Ile Leu Pro Gln Lys Gly Leu Gly Pro Asp Gly Asn Phe
        275                 280                 285

Leu Arg Ala Ser Gln Leu Asn Pro Leu Asn Phe Arg Gln Ala Ile Ser
290                 295                 300

Ser Phe
305

<210> SEQ ID NO 5
<211> LENGTH: 1095
<212> TYPE: DNA
<213> ORGANISM: Lycopersicon esculentum
<220> FEATURE:
<221> NAME/KEY: CDS
<222> LOCATION: (1)..(1095)

<400> SEQUENCE: 5 atg gtt gag ttc ttg caa agc tca att gga atc att cac aga aac cat     48
Met Val Glu Phe Leu Gln Ser Ser Ile Gly Ile Ile His Arg Asn His
1               5                   10                  15 gct gag agt atc acc aca tat atc aga aag agc gtg gat gaa gag ttg     96
Ala Glu Ser Ile Thr Thr Tyr Ile Arg Lys Ser Val Asp Glu Glu Leu
            20                  25                  30
```

-continued

```
aag gag aat aac tca gat tcc aat gtg aag tca aca caa aag aaa cga    144
Lys Glu Asn Asn Ser Asp Ser Asn Val Lys Ser Thr Gln Lys Lys Arg
        35                  40                  45 ctt act ttc tgt gtt gag gga aat att agt gtt gga aaa aca acc ttt    192
Leu Thr Phe Cys Val Glu Gly Asn Ile Ser Val Gly Lys Thr Thr Phe
 50                  55                  60 ctg cag aga ata gct aat gag aca ctt gaa ttg caa gat ctt gtt gaa    240
Leu Gln Arg Ile Ala Asn Glu Thr Leu Glu Leu Gln Asp Leu Val Glu
 65                  70                  75                  80 ata gtt ccc gaa cct att gcc aag tgg cag gat att ggg cca gat cac    288
Ile Val Pro Glu Pro Ile Ala Lys Trp Gln Asp Ile Gly Pro Asp His
                 85                  90                  95 ttt aac ata tta gat gca ttc tat gcg gaa cca caa aga tat gct tac    336
Phe Asn Ile Leu Asp Ala Phe Tyr Ala Glu Pro Gln Arg Tyr Ala Tyr
            100                 105                 110 aca ttt caa aac tat gtt ttt gta aca agg gtt atg cag gag aga gaa    384
Thr Phe Gln Asn Tyr Val Phe Val Thr Arg Val Met Gln Glu Arg Glu
        115                 120                 125 tca tct ggt ggt atc agg ccc ctc agg ttg atg gag aga agt gtg ttc    432
Ser Ser Gly Gly Ile Arg Pro Leu Arg Leu Met Glu Arg Ser Val Phe
130                 135                 140 agt gac agg atg gtc ttt gtg aga gct gtt cat gaa gca aac tgg atg    480
Ser Asp Arg Met Val Phe Val Arg Ala Val His Glu Ala Asn Trp Met
145                 150                 155                 160 aat gag atg gag atc agc att tat gac tca tgg ttt gac ccg gtt gtt    528
Asn Glu Met Glu Ile Ser Ile Tyr Asp Ser Trp Phe Asp Pro Val Val
                165                 170                 175 tca act ttg cct gga ctc att ccc gat ggt ttt att tat ctt aga gca    576
Ser Thr Leu Pro Gly Leu Ile Pro Asp Gly Phe Ile Tyr Leu Arg Ala
            180                 185                 190 agc cct gac aca tgt cac aag aga atg atg ttg cgt aag aga aca gaa    624
Ser Pro Asp Thr Cys His Lys Arg Met Met Leu Arg Lys Arg Thr Glu
        195                 200                 205 gaa ggc gga gtt tcc ttg gaa tat ctg cga ggg ttg cat gag aag cat    672
Glu Gly Gly Val Ser Leu Glu Tyr Leu Arg Gly Leu His Glu Lys His
210                 215                 220 gaa agc tgg ctt ttc cca ttt gaa agt gga aat cat ggg gta ttg tct    720
Glu Ser Trp Leu Phe Pro Phe Glu Ser Gly Asn His Gly Val Leu Ser
225                 230                 235                 240 gtc agc gag cta ccc ctt aac ttt gac aaa tct gta ccc cca gaa ata    768
Val Ser Glu Leu Pro Leu Asn Phe Asp Lys Ser Val Pro Pro Glu Ile
                245                 250                 255 agg gat cgt gtt ttt tat ctg gaa ggc aat cac atg cac ccg agt att    816
Arg Asp Arg Val Phe Tyr Leu Glu Gly Asn His Met His Pro Ser Ile
            260                 265                 270 caa aag gtt cct gcg ttg gtt ctc gac tgc gag cct aac att gac ttt    864
Gln Lys Val Pro Ala Leu Val Leu Asp Cys Glu Pro Asn Ile Asp Phe
        275                 280                 285 aac aga gat att gaa gca aag agg cag tat gct cgt caa gtt gct gat    912
Asn Arg Asp Ile Glu Ala Lys Arg Gln Tyr Ala Arg Gln Val Ala Asp
290                 295                 300 ttt ttc gag ttt gta aaa aag aag caa gaa gtc atg cca gga gct gga    960
Phe Phe Glu Phe Val Lys Lys Lys Gln Glu Val Met Pro Gly Ala Gly
305                 310                 315                 320 gaa gaa cag cct aag ggc aat caa gca ccg gtg atg ctg cct caa aat    1008
Glu Glu Gln Pro Lys Gly Asn Gln Ala Pro Val Met Leu Pro Gln Asn
                325                 330                 335 gga ggt ttg tgg gta cct ggt ggc aaa ttc tca gaa tca aca ctg aac    1056
Gly Gly Leu Trp Val Pro Gly Gly Lys Phe Ser Glu Ser Thr Leu Asn
```

-continued

```
                340                 345                 350
ttg gat ttc aga cga aat atg tca ttc atg tca cac tag              1095
Leu Asp Phe Arg Arg Asn Met Ser Phe Met Ser His
        355                 360
```

<210> SEQ ID NO 6
<211> LENGTH: 364
<212> TYPE: PRT
<213> ORGANISM: Lycopersicon esculentum

<400> SEQUENCE: 6

Met Val Glu Phe Leu Gln Ser Ser Ile Gly Ile Ile His Arg Asn His
1               5                   10                  15

Ala Glu Ser Ile Thr Thr Tyr Ile Arg Lys Ser Val Asp Glu Glu Leu
            20                  25                  30

Lys Glu Asn Asn Ser Asp Ser Asn Val Lys Ser Thr Gln Lys Lys Arg
        35                  40                  45

Leu Thr Phe Cys Val Glu Gly Asn Ile Ser Val Gly Lys Thr Thr Phe
    50                  55                  60

Leu Gln Arg Ile Ala Asn Glu Thr Leu Glu Leu Gln Asp Leu Val Glu
65                  70                  75                  80

Ile Val Pro Glu Pro Ile Ala Lys Trp Gln Asp Ile Gly Pro Asp His
                85                  90                  95

Phe Asn Ile Leu Asp Ala Phe Tyr Ala Glu Pro Gln Arg Tyr Ala Tyr
            100                 105                 110

Thr Phe Gln Asn Tyr Val Phe Val Thr Arg Val Met Gln Glu Arg Glu
        115                 120                 125

Ser Ser Gly Gly Ile Arg Pro Leu Arg Leu Met Glu Arg Ser Val Phe
    130                 135                 140

Ser Asp Arg Met Val Phe Val Arg Ala Val His Glu Ala Asn Trp Met
145                 150                 155                 160

Asn Glu Met Glu Ile Ser Ile Tyr Asp Ser Trp Phe Asp Pro Val Val
                165                 170                 175

Ser Thr Leu Pro Gly Leu Ile Pro Asp Gly Phe Ile Tyr Leu Arg Ala
            180                 185                 190

Ser Pro Asp Thr Cys His Lys Arg Met Met Leu Arg Lys Arg Thr Glu
        195                 200                 205

Glu Gly Gly Val Ser Leu Glu Tyr Leu Arg Gly Leu His Glu Lys His
    210                 215                 220

Glu Ser Trp Leu Phe Pro Phe Glu Ser Gly Asn His Gly Val Leu Ser
225                 230                 235                 240

Val Ser Glu Leu Pro Leu Asn Phe Asp Lys Ser Val Pro Pro Glu Ile
                245                 250                 255

Arg Asp Arg Val Phe Tyr Leu Glu Gly Asn His Met His Pro Ser Ile
            260                 265                 270

Gln Lys Val Pro Ala Leu Val Leu Asp Cys Glu Pro Asn Ile Asp Phe
        275                 280                 285

Asn Arg Asp Ile Glu Ala Lys Arg Gln Tyr Ala Arg Gln Val Ala Asp
    290                 295                 300

Phe Phe Glu Phe Val Lys Lys Gln Glu Val Met Pro Gly Ala Gly
305                 310                 315                 320

Glu Glu Gln Pro Lys Gly Asn Gln Ala Pro Val Met Leu Pro Gln Asn
                325                 330                 335

Gly Gly Leu Trp Val Pro Gly Lys Phe Ser Glu Ser Thr Leu Asn
            340                 345                 350

-continued

```
Leu Asp Phe Arg Arg Asn Met Ser Phe Met Ser His
        355                 360

<210> SEQ ID NO 7
<211> LENGTH: 816
<212> TYPE: DNA
<213> ORGANISM: Zea mays
<220> FEATURE:
<221> NAME/KEY: CDS
<222> LOCATION: (1)..(816)

<400> SEQUENCE: 7 ttc aat gta ctt gat gct ttc tat gca gag cca cag agg tat gca tac      48
Phe Asn Val Leu Asp Ala Phe Tyr Ala Glu Pro Gln Arg Tyr Ala Tyr
1               5                   10                  15 acc ttc cag aat tat gta ttt gtg aca agg gtc atg caa gag aag gaa      96
Thr Phe Gln Asn Tyr Val Phe Val Thr Arg Val Met Gln Glu Lys Glu
            20                  25                  30 tct gcg tgt gga ata aaa cct ctt agg ctg atg gaa aga agc gtt ttc     144
Ser Ala Cys Gly Ile Lys Pro Leu Arg Leu Met Glu Arg Ser Val Phe
        35                  40                  45 agt gat cga atg gtt ttt gtt cgt gct gtg cat gaa gca aac tgg atg     192
Ser Asp Arg Met Val Phe Val Arg Ala Val His Glu Ala Asn Trp Met
    50                  55                  60 aac gag atg gaa atc agc att tat gac tct tgg ttt gac cca gtt gtg     240
Asn Glu Met Glu Ile Ser Ile Tyr Asp Ser Trp Phe Asp Pro Val Val
65                  70                  75                  80 tca tca ctc cca ggt ctt gta cct gat ggt ttt att tat cta aga gct     288
Ser Ser Leu Pro Gly Leu Val Pro Asp Gly Phe Ile Tyr Leu Arg Ala
                85                  90                  95 agc cct gat act tgt cac aaa aga atg atg gtg cga aaa aga tca gag     336
Ser Pro Asp Thr Cys His Lys Arg Met Met Val Arg Lys Arg Ser Glu
            100                 105                 110 gag gct ggt gtt act ctt gat tac ctt cga ggt ttg cat gag aaa cat     384
Glu Ala Gly Val Thr Leu Asp Tyr Leu Arg Gly Leu His Glu Lys His
        115                 120                 125 gag agc tgg tta ctt cca tcc aag gga gga ggt tct ggc gtg ttg tcc     432
Glu Ser Trp Leu Leu Pro Ser Lys Gly Gly Gly Ser Gly Val Leu Ser
    130                 135                 140 atc agt cag ctt cca gtt cat atg gag ggc tcc ctg cat gcg gat ata     480
Ile Ser Gln Leu Pro Val His Met Glu Gly Ser Leu His Ala Asp Ile
145                 150                 155                 160 cga gat agg gta ttc tac ttg gaa gga gat cac atg cat tca agt atc     528
Arg Asp Arg Val Phe Tyr Leu Glu Gly Asp His Met His Ser Ser Ile
                165                 170                 175 cag aag gtt cct gct ctt atc ctg gac tgt gaa cat gac att gat ttt     576
Gln Lys Val Pro Ala Leu Ile Leu Asp Cys Glu His Asp Ile Asp Phe
            180                 185                 190 aac aag gac atc gaa gcc aaa cga caa tat gct cgg caa gtt gcg gag     624
Asn Lys Asp Ile Glu Ala Lys Arg Gln Tyr Ala Arg Gln Val Ala Glu
        195                 200                 205 ttc ttt gac ttt gtg aag aaa aag aag gaa tct ctt aca gca gag tca     672
Phe Phe Asp Phe Val Lys Lys Lys Lys Glu Ser Leu Thr Ala Glu Ser
    210                 215                 220 gag acg gct gat ggt gat aag agt ata aac aaa cag att gtg ctg ccg     720
Glu Thr Ala Asp Gly Asp Lys Ser Ile Asn Lys Gln Ile Val Leu Pro
225                 230                 235                 240 cac gga ggt ggt ttg tgg gtg ccc gga agc agc ccg tta cca gaa tca     768
His Gly Gly Gly Leu Trp Val Pro Gly Ser Ser Pro Leu Pro Glu Ser
                245                 250                 255
```

```
gct cta aaa tca ttt gat ttc agg aga acg atg tct tcc tcg act taa      816
Ala Leu Lys Ser Phe Asp Phe Arg Arg Thr Met Ser Ser Ser Thr
    260             265                 270
```

<210> SEQ ID NO 8
<211> LENGTH: 271
<212> TYPE: PRT
<213> ORGANISM: Zea mays

<400> SEQUENCE: 8

```
Phe Asn Val Leu Asp Ala Phe Tyr Ala Glu Pro Gln Arg Tyr Ala Tyr
1               5                   10                  15

Thr Phe Gln Asn Tyr Val Phe Val Thr Arg Val Met Gln Glu Lys Glu
            20                  25                  30

Ser Ala Cys Gly Ile Lys Pro Leu Arg Leu Met Glu Arg Ser Val Phe
        35                  40                  45

Ser Asp Arg Met Val Phe Val Arg Ala Val His Glu Ala Asn Trp Met
    50                  55                  60

Asn Glu Met Glu Ile Ser Ile Tyr Asp Ser Trp Phe Asp Pro Val Val
65                  70                  75                  80

Ser Ser Leu Pro Gly Leu Val Pro Asp Gly Phe Ile Tyr Leu Arg Ala
                85                  90                  95

Ser Pro Asp Thr Cys His Lys Arg Met Met Val Arg Lys Arg Ser Glu
            100                 105                 110

Glu Ala Gly Val Thr Leu Asp Tyr Leu Arg Gly Leu His Glu Lys His
        115                 120                 125

Glu Ser Trp Leu Leu Pro Ser Lys Gly Gly Ser Gly Val Leu Ser
    130                 135                 140

Ile Ser Gln Leu Pro Val His Met Glu Gly Ser Leu His Ala Asp Ile
145                 150                 155                 160

Arg Asp Arg Val Phe Tyr Leu Glu Gly Asp His Met His Ser Ser Ile
                165                 170                 175

Gln Lys Val Pro Ala Leu Ile Leu Asp Cys Glu His Asp Ile Asp Phe
            180                 185                 190

Asn Lys Asp Ile Glu Ala Lys Arg Gln Tyr Ala Arg Gln Val Ala Glu
        195                 200                 205

Phe Phe Asp Phe Val Lys Lys Lys Glu Ser Leu Thr Ala Glu Ser
    210                 215                 220

Glu Thr Ala Asp Gly Asp Lys Ser Ile Asn Lys Gln Ile Val Leu Pro
225                 230                 235                 240

His Gly Gly Gly Leu Trp Val Pro Gly Ser Ser Pro Leu Pro Glu Ser
                245                 250                 255

Ala Leu Lys Ser Phe Asp Phe Arg Thr Met Ser Ser Ser Thr
            260                 265                 270
```

<210> SEQ ID NO 9
<211> LENGTH: 217
<212> TYPE: DNA
<213> ORGANISM: Oryza sativa
<220> FEATURE:
<221> NAME/KEY: CDS
<222> LOCATION: (2)..(217)

<400> SEQUENCE: 9

```
g caa tat gct cag caa gtt gca gaa ttc ttt caa ttt gtg aag aaa aag     49
  Gln Tyr Ala Gln Gln Val Ala Glu Phe Phe Gln Phe Val Lys Lys Lys
  1               5                   10                  15 aag gaa gct cca tct gaa caa aca agc act gac aag aac cgt atc aat      97
```

```
Lys Glu Ala Pro Ser Glu Gln Thr Ser Thr Asp Lys Asn Arg Ile Asn
            20                  25                  30 cca cag atc atg ctt cct cac aaa ggc gga ttg tgg gtt cct gat gga    145
Pro Gln Ile Met Leu Pro His Lys Gly Gly Leu Trp Val Pro Asp Gly
        35                  40                  45 aga aac cct ttc tca gga tct gct atg aat ctg aac ttc aga aga gcc    193
Arg Asn Pro Phe Ser Gly Ser Ala Met Asn Leu Asn Phe Arg Arg Ala
    50                  55                  60 atg tct tcc tat ctc tcg aca tag                                    217
Met Ser Ser Tyr Leu Ser Thr
65                  70
```

<210> SEQ ID NO 10
<211> LENGTH: 71
<212> TYPE: PRT
<213> ORGANISM: Oryza sativa

<400> SEQUENCE: 10

```
Gln Tyr Ala Gln Gln Val Ala Glu Phe Phe Gln Phe Val Lys Lys Lys
1               5                   10                  15

Lys Glu Ala Pro Ser Glu Gln Thr Ser Thr Asp Lys Asn Arg Ile Asn
            20                  25                  30

Pro Gln Ile Met Leu Pro His Lys Gly Gly Leu Trp Val Pro Asp Gly
        35                  40                  45

Arg Asn Pro Phe Ser Gly Ser Ala Met Asn Leu Asn Phe Arg Arg Ala
    50                  55                  60

Met Ser Ser Tyr Leu Ser Thr
65                  70
```

<210> SEQ ID NO 11
<211> LENGTH: 1095
<212> TYPE: DNA
<213> ORGANISM: Oryza sativa
<220> FEATURE:
<221> NAME/KEY: CDS
<222> LOCATION: (1)..(1095)

<400> SEQUENCE: 11

```
atg gtt gag ttc ttg caa agt tct gtt ggc atc ata cac aag aat cat    48
Met Val Glu Phe Leu Gln Ser Ser Val Gly Ile Ile His Lys Asn His
1               5                   10                  15 gct gag agt ata act ttg ttc att aaa gaa agt gtt gat gaa gag ctg    96
Ala Glu Ser Ile Thr Leu Phe Ile Lys Glu Ser Val Asp Glu Glu Leu
            20                  25                  30 aaa gga act gac tca cca aat gtt tcc aaa aat aag agg ctg acc ttt    144
Lys Gly Thr Asp Ser Pro Asn Val Ser Lys Asn Lys Arg Leu Thr Phe
        35                  40                  45 tgt gtg gaa ggg aac atc agt gtc gga aaa act aca ttc ctt caa aga    192
Cys Val Glu Gly Asn Ile Ser Val Gly Lys Thr Thr Phe Leu Gln Arg
    50                  55                  60 att gcc aat gag acc atc gaa tta cgt gac ctt gta gag ata gtg cct    240
Ile Ala Asn Glu Thr Ile Glu Leu Arg Asp Leu Val Glu Ile Val Pro
65                  70                  75                  80 gaa cct att gct aaa tgg caa gat gtt ggc cct gat cac ttc aac ata    288
Glu Pro Ile Ala Lys Trp Gln Asp Val Gly Pro Asp His Phe Asn Ile
                85                  90                  95 ctt gat gct ttc tat gct gag cca cag agg tat gca tac act ttc cag    336
Leu Asp Ala Phe Tyr Ala Glu Pro Gln Arg Tyr Ala Tyr Thr Phe Gln
            100                 105                 110 aat tat gtg ttt gtt aca agg gtc atg caa gag aag gaa tct tca agt    384
Asn Tyr Val Phe Val Thr Arg Val Met Gln Glu Lys Glu Ser Ser Ser
```

|  |  |  |  |  |  |  |  |  |  |  |  |  |  |  |  |
|---|---|---|---|---|---|---|---|---|---|---|---|---|---|---|---|
|  |  | 115 |  |  |  | 120 |  |  |  | 125 |  |  |  |  |  |

```
ggc ata aag cct ctc agg ttg atg gaa aga agt gtt ttc agt gat aga       432
Gly Ile Lys Pro Leu Arg Leu Met Glu Arg Ser Val Phe Ser Asp Arg
        130                 135                 140 atg gta ttt gtt cgt gct gtc cat gaa gcc aac tgg atg aac gag atg       480
Met Val Phe Val Arg Ala Val His Glu Ala Asn Trp Met Asn Glu Met
145                 150                 155                 160 gag atc agc atc tat gac tcc tgg ttt gac cca gtg gtg tca tca ctc       528
Glu Ile Ser Ile Tyr Asp Ser Trp Phe Asp Pro Val Val Ser Ser Leu
                165                 170                 175 cca gga ctt att cca gat ggt ttt att tat cta aga gct agt ccc gac       576
Pro Gly Leu Ile Pro Asp Gly Phe Ile Tyr Leu Arg Ala Ser Pro Asp
        180                 185                 190 act tgc cac aaa aga atg atg gtt cgg aaa aga tct gaa gag ggt ggt       624
Thr Cys His Lys Arg Met Met Val Arg Lys Arg Ser Glu Glu Gly Gly
                195                 200                 205 gtt act ctt gat tac ctt cga ggt ttg cat gag aaa cat gag agc tgg       672
Val Thr Leu Asp Tyr Leu Arg Gly Leu His Glu Lys His Glu Ser Trp
210                 215                 220 ctg ctt cct tcc aaa gga caa ggt cct ggt gta tta tcg gtc agt caa       720
Leu Leu Pro Ser Lys Gly Gln Gly Pro Gly Val Leu Ser Val Ser Gln
225                 230                 235                 240 gtt cca gtc cat atg gag ggc tct ttg cct ccg gat ata aga gaa cga       768
Val Pro Val His Met Glu Gly Ser Leu Pro Pro Asp Ile Arg Glu Arg
                245                 250                 255 gta ttc tac tta gaa gga gat cat atg cat tct agt atc cag aag gtt       816
Val Phe Tyr Leu Glu Gly Asp His Met His Ser Ser Ile Gln Lys Val
        260                 265                 270 cct gct ctg gtc ctc gac tgc gaa cat gac att gat ttt aac aag gat       864
Pro Ala Leu Val Leu Asp Cys Glu His Asp Ile Asp Phe Asn Lys Asp
        275                 280                 285 att gaa gcc aaa cga cag tat gcc cga caa gtt gcg gag ttc ttt gaa       912
Ile Glu Ala Lys Arg Gln Tyr Ala Arg Gln Val Ala Glu Phe Phe Glu
        290                 295                 300 ttt gta aag aaa aag aaa gaa gat cct tct gcg gag tca agt ggt ggt       960
Phe Val Lys Lys Lys Lys Glu Asp Pro Ser Ala Glu Ser Ser Gly Gly
305                 310                 315                 320 gat aag agt acc aac aaa cag att atg ctt ccc cac aga ggt ggt ttg      1008
Asp Lys Ser Thr Asn Lys Gln Ile Met Leu Pro His Arg Gly Gly Leu
                325                 330                 335 tgg gtt ccc gaa ggt aac cct tta cca gga tct gct ctg aac tct ctg      1056
Trp Val Pro Glu Gly Asn Pro Leu Pro Gly Ser Ala Leu Asn Ser Leu
        340                 345                 350 gat ttc aga aga gca atg tct tcc ttc ctc tca gct tag                   1095
Asp Phe Arg Arg Ala Met Ser Ser Phe Leu Ser Ala
        355                 360

<210> SEQ ID NO 12
<211> LENGTH: 364
<212> TYPE: PRT
<213> ORGANISM: Oryza sativa

<400> SEQUENCE: 12

Met Val Glu Phe Leu Gln Ser Ser Val Gly Ile Ile His Lys Asn His
1               5                   10                  15

Ala Glu Ser Ile Thr Leu Phe Ile Lys Glu Ser Val Asp Glu Glu Leu
            20                  25                  30

Lys Gly Thr Asp Ser Pro Asn Val Ser Lys Asn Lys Arg Leu Thr Phe
        35                  40                  45
```

```
Cys Val Glu Gly Asn Ile Ser Val Gly Lys Thr Thr Phe Leu Gln Arg
 50                  55                  60

Ile Ala Asn Glu Thr Ile Glu Leu Arg Asp Leu Val Glu Ile Val Pro
 65                  70                  75                  80

Glu Pro Ile Ala Lys Trp Gln Asp Val Gly Pro Asp His Phe Asn Ile
                 85                  90                  95

Leu Asp Ala Phe Tyr Ala Glu Pro Gln Arg Tyr Ala Tyr Thr Phe Gln
            100                 105                 110

Asn Tyr Val Phe Val Thr Arg Val Met Gln Glu Lys Glu Ser Ser Ser
        115                 120                 125

Gly Ile Lys Pro Leu Arg Leu Met Glu Arg Ser Val Phe Ser Asp Arg
    130                 135                 140

Met Val Phe Val Arg Ala Val His Glu Ala Asn Trp Met Asn Glu Met
145                 150                 155                 160

Glu Ile Ser Ile Tyr Asp Ser Trp Phe Asp Pro Val Val Ser Ser Leu
                165                 170                 175

Pro Gly Leu Ile Pro Asp Gly Phe Ile Tyr Leu Arg Ala Ser Pro Asp
            180                 185                 190

Thr Cys His Lys Arg Met Met Val Arg Lys Arg Ser Glu Glu Gly Gly
        195                 200                 205

Val Thr Leu Asp Tyr Leu Arg Gly Leu His Glu Lys His Glu Ser Trp
    210                 215                 220

Leu Leu Pro Ser Lys Gly Gln Gly Pro Gly Val Leu Ser Val Ser Gln
225                 230                 235                 240

Val Pro Val His Met Glu Gly Ser Leu Pro Pro Asp Ile Arg Glu Arg
                245                 250                 255

Val Phe Tyr Leu Glu Gly Asp His Met His Ser Ser Ile Gln Lys Val
            260                 265                 270

Pro Ala Leu Val Leu Asp Cys Glu His Asp Ile Asp Phe Asn Lys Asp
        275                 280                 285

Ile Glu Ala Lys Arg Gln Tyr Ala Arg Gln Val Ala Glu Phe Phe Glu
    290                 295                 300

Phe Val Lys Lys Lys Lys Glu Asp Pro Ser Ala Glu Ser Ser Gly Gly
305                 310                 315                 320

Asp Lys Ser Thr Asn Lys Gln Ile Met Leu Pro His Arg Gly Gly Leu
                325                 330                 335

Trp Val Pro Glu Gly Asn Pro Leu Pro Gly Ser Ala Leu Asn Ser Leu
            340                 345                 350

Asp Phe Arg Arg Ala Met Ser Ser Phe Leu Ser Ala
        355                 360

<210> SEQ ID NO 13
<211> LENGTH: 42
<212> TYPE: DNA
<213> ORGANISM: Artificial sequence
<220> FEATURE:
<223> OTHER INFORMATION: PCR primer sequence

<400> SEQUENCE: 13
tatcgcggat ccatggttga gttcttgcaa agctcaattg ga            42

<210> SEQ ID NO 14
<211> LENGTH: 41
<212> TYPE: DNA
<213> ORGANISM: artificial sequence
<220> FEATURE:
<223> OTHER INFORMATION: PCR primer sequence
```

<400> SEQUENCE: 14
ccggaattcg tcgacttagt gagacatgaa tgacatattt c                41

<210> SEQ ID NO 15
<211> LENGTH: 42
<212> TYPE: DNA
<213> ORGANISM: Artificial sequence
<220> FEATURE:
<223> OTHER INFORMATION: PCR primer sequence

<400> SEQUENCE: 15
tatcgcggat ccgtgaagtc aacacaaaag aaacgactta ct                42

<210> SEQ ID NO 16
<211> LENGTH: 42
<212> TYPE: DNA
<213> ORGANISM: Artificial sequence
<220> FEATURE:
<223> OTHER INFORMATION: PCR primer sequence

<400> SEQUENCE: 16
ccggaatcct taagcaactt gacgagcata ctgcctcttt gc                42

<210> SEQ ID NO 17
<211> LENGTH: 39
<212> TYPE: DNA
<213> ORGANISM: artificial sequence
<220> FEATURE:
<223> OTHER INFORMATION: PCR primer sequence

<400> SEQUENCE: 17
cgcggatcca tggttgatta tcttaggagc tctgttggg                39

<210> SEQ ID NO 18
<211> LENGTH: 40
<212> TYPE: DNA
<213> ORGANISM: Artificial sequence
<220> FEATURE:
<223> OTHER INFORMATION: PCR primer sequence

<400> SEQUENCE: 18
ccggaattct cacgcagacg gtctagtgag gagtgacttg                40

<210> SEQ ID NO 19
<211> LENGTH: 31
<212> TYPE: DNA
<213> ORGANISM: Artificial sequence
<220> FEATURE:
<223> OTHER INFORMATION: PCR-primer

<400> SEQUENCE: 19
cgcggatcca tggcttcgta ccccggccat c                31

<210> SEQ ID NO 20
<211> LENGTH: 33
<212> TYPE: DNA
<213> ORGANISM: Artificial sequence
<220> FEATURE:
<223> OTHER INFORMATION: PCR-primer

<400> SEQUENCE: 20
ccggaattct tagttagcct cccccatctc ccg                33

<210> SEQ ID NO 21

-continued

```
<211> LENGTH: 34
<212> TYPE: DNA
<213> ORGANISM: Artificial Sequence
<220> FEATURE:
<223> OTHER INFORMATION: Primer sequence

<400> SEQUENCE: 21
tccctcgagc gccatggttg attatcttag gagc                                34

<210> SEQ ID NO 22
<211> LENGTH: 32
<212> TYPE: DNA
<213> ORGANISM: Artificial Sequence
<220> FEATURE:
<223> OTHER INFORMATION: Primer sequence

<400> SEQUENCE: 22
cgggatcctc acgcagacgg tctagtgagg ag                                  32

<210> SEQ ID NO 23
<211> LENGTH: 34
<212> TYPE: DNA
<213> ORGANISM: Artificial Sequence
<220> FEATURE:
<223> OTHER INFORMATION: Primer sequence

<400> SEQUENCE: 23
tccctcgagc gccatggttg agttcttgca aagc                                34

<210> SEQ ID NO 24
<211> LENGTH: 34
<212> TYPE: DNA
<213> ORGANISM: Artificial Sequence
<220> FEATURE:
<223> OTHER INFORMATION: Primer sequence

<400> SEQUENCE: 24
cgggatcctt agtgagacat gaatgacata tttc                                34
```